(12) United States Patent
Ezratty et al.

(10) Patent No.: US 7,330,794 B2
(45) Date of Patent: Feb. 12, 2008

(54) WATER MONITORING SYSTEM USING BIVALVE MOLLUSKS

(75) Inventors: Jason Ezratty, New York, NY (US); Robert Morgan, State College, PA (US); David Eddy, Tarentum, PA (US); Donald Morgan, Woodinville, WA (US)

(73) Assignee: Aqueous Solutions, Inc., New York, NY (US)

( * ) Notice: Subject to any disclaimer, the term of this patent is extended or adjusted under 35 U.S.C. 154(b) by 672 days.

(21) Appl. No.: 10/343,660

(22) PCT Filed: Jul. 30, 2001

(86) PCT No.: PCT/US01/23857

§ 371 (c)(1),
(2), (4) Date: Feb. 3, 2003

(87) PCT Pub. No.: WO02/10710

PCT Pub. Date: Feb. 7, 2002

(65) Prior Publication Data

US 2003/0211041 A1    Nov. 13, 2003

Related U.S. Application Data

(63) Continuation-in-part of application No. 09/631,045, filed on Aug. 1, 2000, now abandoned.

(51) Int. Cl.
*G06F 19/00* (2006.01)
*C12Q 1/00* (2006.01)
*C12N 5/02* (2006.01)
*G01F 1/12* (2006.01)

(52) U.S. Cl. .............................. 702/19; 702/100; 702/1; 435/4; 435/429

(58) Field of Classification Search ...................... None
See application file for complete search history.

(56) References Cited

U.S. PATENT DOCUMENTS

| | | |
|---|---|---|
| 3,100,473 A | 8/1963 | Kissel |
| 4,626,992 A | 12/1986 | Greaves et al. |
| 4,686,504 A | 8/1987 | German |
| 4,723,511 A | 2/1988 | Solman et al. |
| 4,888,703 A | 12/1989 | Baba et al. |
| 5,140,855 A | 8/1992 | Gruber |
| 5,265,619 A | 11/1993 | Comby et al. |
| 5,307,052 A | 4/1994 | Harrison et al. |
| 5,804,705 A | 9/1998 | Florion et al. |
| 5,903,305 A | 5/1999 | Yamamoto |
| 6,289,328 B2 | 9/2001 | Shaffer |

OTHER PUBLICATIONS

Kramer et. al, The valve movement response of mussels: a tool in biological monitoring, Hydrobiologia, 188/189: 433-443, 1989.*

Kramer, Kees J.M., et al. Hydrobiologia 188/189: p. 433-443, (1989).
Slooff, W., et al. "Detection Limits of a Biological Monitoring System for Chemical Water Pollution Based on Mussel Activity". Bull. Environ. Contam. Toxicol. 30, p. 400-405 (1983).
Allen, H. Joel, et al. "A Behavorial Model for Corbicula fluminea and its use in a Real-Time Biomonitoring System". (1997).
Waller, W. Tom, et al. "TR-172 The Use of Remotely Sensed Bioelectric Action Potentials to Evaluate Episodic Toxicity Events and Ambient Toxicity". (1996).
Jenner, H.A., et al. "A New System for the Detection of Valve-Movement Response of Bivalves". Kema Scientific & Technical Reports 7 (2): pp. 91-98 (1989).
Jenner, Henk A., et al. "Monitoring Water Quality with Bihalves". Feb. 1991.
Delta Consult. "The Mosselmonitor, an Early Warning System". Biological Water Pollution Monitor. Feb. 1991.
Varanka. "Effect of Mosquito Killer Insecticides on Freshwater Mussels", Comp. Biochem. Physiol. vol. 86C, No. 1, pp. 157-162. (1987).
Morgan, E.L., et al. "Automated Multispecies Biosensing System and Development: Advances In Real-Time Water Quality Monitoring". The Biosphere: Problems and Solutions, pp. 297-299. (1982).
Doherty, Francis G., et al. "Valve Closure Responses of the Asiatic Clam *Corbicula fluminea* Exposed to Cadmium and Zinc". Hydrobiologia 153: pp. 159-167 (1987).
Borcherding, Jost. "Another Early Warning System for the Detection of Toxic Discharges in the Aquatic Environment Based on Valve Movements of the Freshwater Mussel *Dreissena polymorpha*". Limnologie aktuell vol. 4 Neumann/Jenner (Eds.): The Zebra Mussel Dreissena polymorhpa. (1992).
Mouabad, A., et al. "Pumping behaviour and filtration rate of the freshwater mussel *Potomida littoralis* as a tool for rapid detection of water contamination". Aquatic Ecology 35: pp. 51-60 (2001).
Eapen, John T., "An Electronic Device to Record Behavioural Activity of Bihalves". Indian Journal of Biology vol. 35, pp. 663-664 (1997).

(Continued)

*Primary Examiner*—Lori Clow
*Assistant Examiner*—Jason Sims
(74) *Attorney, Agent, or Firm*—Tiajoloff & Kelly

(57) ABSTRACT

A toxicant detection system comprises at least one watertight chamber containing a mollusk. Water to be screened is introduced into the chamber. The mollusk is preferably supported on a mounting structure which facilitates quick mounting of the mollusk in the device, comprising a releasable element affixed to the shell of the mollusk, e.g., a bolt which is screwed into a nut affixed to the mollusk's shell. A sensing apparatus is provided which includes a movable member supported in the chamber so that it engages the shell of the mollusk, and moves when the shell opens and closes. The sensing apparatus detects the position of the mollusk shell based on the position of the movable member. The sensing apparatus preferably includes a Hall effect transducer which co-acts with a magnet carried on the movable member. The system allows for accurate readings of the small movements of the mollusk shell which aid in detecting toxicants, and also provides for installation of mollusks of varying sizes, without the need to move components of the standard configuration of the chamber. Methods and systems for detecting or identifying a toxicant in water being screened are also described.

23 Claims, 21 Drawing Sheets

OTHER PUBLICATIONS

Miller, Andrew C., et al., "A Shell Gape Monitor to Study Effects of Physical Disturbance on Freshwater Mussels". Journal of Freshwater Ecology, vol. 14, No. 2 (1999).

Ham, Kenneth D., et al. "Effect of Fluctuating Low-Level Chlorine Concentrations on Valve-Movement Behavior of the Asiatic Clam (*Corbicula fluminea*)". Environmental Toxicology and Chemistry, vol. 13, No. 3, pp. 493-498 (1994).

Waller et al. "The Use of Remotely Sensed Bioelectric Action Potentials to Evaluate Episodic Toxicity Events and Ambient Toxicity" Texas Water Resources Institute, Jan. 1996.

Abstract, Eapen, "An Electronic Device to Record Behavioural Activity of Bivalves", Indian Journal of Biology, vol. 35, p. 663-664 (1997).

Abstract, Miller et al. "A shell gape monitor to study the effects of physical disturbance on freshwater mussels", J. of Freshwater Ecology 14(2) p. 241-247, Jun. 1999.

Abstract, Mouabad et al., Pumping behaviour and filtration rate of the freshwater mussel *Potomida littoralis* as a tool for rapid detection of water contamination Aquatic Ecology, 35 (1) p. 51-60, Mar. 2001.

Abstract, Bouget et al., "Biological monitoring of water quality in an estuarian shellfish area, using a biosensor recording valve movements of oysters and mussels", Tech. Sciences Methodes, Genie Urban-Genie Rural (1997).

* cited by examiner

WATER MONITORING SYSTEM USING BIVALVE MOLLUSKS

This application is a continuation-in-part of application Ser. No. 09/631,045 field Agu. 1, 2000, now abandoned.

BACKGROUND OF THE INVENTION

1. Field of the Invention

This invention relates to the field of monitoring water quality and, more particularly, to monitoring water quality using bivalve mollusks to detect toxicants.

2. Discussion of the Prior Art

Various organisms have been used to aid in the detection of low-concentration waterborne toxins or toxicants (hereinafter both being referred to as "toxicants" in the broadest sense of the word). Systems for testing water quality using fish, for instance, have been known for some time. For example, in U.S. Pat. No. 4,626,992 to Greaves et al, a video camera monitors the swimming of the fish, and toxicity in the water is indicated by significant changes in swimming behavior. Another system of this type is described in U.S. Pat. No. 4,723,511 to Solman et al., wherein electrodes monitor electric currents generated by fish in a tank of water being tested.

Systems which use fish, however, have a number of disadvantages. Usually, the fish are free to move in the system, which introduces ambiguous behavioral variables. The fish also need to be fed which is periodic and unpredictable. Also the fish must be otherwise cared for, resulting in a high maintenance system which is unsuitable for long-term unattended operation.

Systems for monitoring water quality using bivalve mollusks have also been suggested in the prior art. Mollusks are particularly sensitive to some pollutants, such as chlorine or sulphuric acid, to metals like copper or cadmium, and to a wide range of organic compounds such as pesticides and hydrocarbons. These systems usually rely on the simple fact that a bivalve keeps its shells open under normal conditions, but closes its shells when a toxicant is detected.

Depending on the species, bivalve mollusks can be long lived with life expectancies of 60 to 80 years. Because the animals are filter feeders, and therefore self feeding, deriving all their nutrition and oxygen from the ambient water, a single cohort could theoretically be used for many years in an in situ monitoring system. To ensure peak physical condition and maximum sensitivity in detecting toxicants, however, bivalves in the monitoring system should be routinely changed at four- to six-month intervals depending on conditions. Also, if exposed to a toxicant, the bivalves should immediately be replaced with naive animals, i.e. mollusks that have not previously been exposed to toxicants.

Mollusk-based detection systems of the prior art, however, are generally not configured for the ready installation or removal of mollusks, which can vary considerably in size, even within a species. There is consequently substantial work required to install and calibrate the sensor system, which in the prior art is effectively built around the individual mollusk.

In addition, systems that detect the presence of toxicants in response to closure of the shell of the mollusk neglect earlier indications of toxicant presence that precede full closure of the shell. This delays the detection of toxicants, especially in lower concentrations. There is also a potential for false negatives or false positives in prior art systems due to a slow or only partial closure of the shell in the presence of a toxicant, due to diurnal behaviors of the mollusk.

SUMMARY OF THE INVENTION

Accordingly, it is an object of the present invention to provide for a reliable and relatively low maintenance water quality monitoring system using one or more bivalve mollusks.

It is also an object of the present invention to provide an apparatus for using bivalve mollusks as detectors of toxicants which detects the movements of the shell with a high degree of accuracy, and wherein the mollusks of varying sizes can readily be installed or removed when necessary.

According to the present invention, at least one watertight chamber containing a mollusk is provided, and water to be screened is introduced into the chamber. A sensing apparatus is provided which includes a movable member supported in the chamber so that it engages the shell of the mollusk, and moves when the shell opens and closes. The sensing apparatus detects the position of the mollusk shell based on the position of the movable member. The system allows for accurate readings of small movements of the mollusk shell which aid in detecting toxicants, and also provides for installation of mollusks of varying sizes, without the need to attach complex structures directly to the shell of the mollusk.

Preferably, the movable member carries a magnet which co-acts with a Hall effect transducer supported on an adjustable structure, which facilitates calibration of the position of the sensor during installation of the mollusk in the device.

In addition, the mollusk is preferably supported on a mounting structure which has a releasable element affixed to the shell of the mollusk, e.g., a bolt which is screwed into a nut affixed to the mollusk's shell by glue, or some other method. This structure facilitates quick mounting of the mollusk in the device.

According to the present invention, the diurnal cycles of the mollusks used to screen water are reduced or eliminated by maintaining the mollusks in a lighted environment at all times.

Other advantages and objects of the present invention will become apparent in the specification here set forth, and the scope of the invention will be set forth in the claims.

DETAILED DESCRIPTION OF THE INVENTION

The system of the present invention is configured to test water for the presence of a variety of toxicants by monitoring bivalve shell movement. Bivalves (clams, mussels, etc.) are mollusks having two hinged shells or valves.

Because bivalves, in their natural environment, are relatively sedentary and immobile, they have had to evolve behaviors to avoid the detrimental effects of toxicants. Normally, bivalves feed, acquire oxygen, and release wastes through tube-like siphons that extend between the shells, and consequently their shells are open most of the time. In the presence of a toxic substance, however, the animals retract the siphons and alter the shell opening (or gape) in an effort to exclude the toxicant.

Depending on the type and level of toxicity, the animals typically may partially or totally close their shells. Certain toxicants may even cause the shells to gape wider than normal as the animals lose muscular control, and in rare extreme cases where a toxicant proves fatal, the death of the animal results in an abnormally wide gape. Generally, movement of the shells can be varied, such as fluttering, or a simpler closing or opening, of the shell. The associated changes in shell gape are relied upon in the system of the present invention.

The invention can monitor fresh or salt waters by using bivalve species appropriate to the application. For freshwater applications, species of choice include members of the family Unionidae, and especially preferred is *Elliptio complanta*. Where they are already established, the ubiquitous pest species *Dreissena polymorpha* (zebra mussel) and *Corbicula manilensis* (Asiatic clam) can be used. For saltwater applications, bivalves as diverse as *Mytilus* species (marine mussels), especially *Mytilus edulus* (blue mussels), *Crassostrea* species (oysters) and species of the family Pectinidae (scallops) as well as others can be used.

a. Overall System Design

Figure 1:
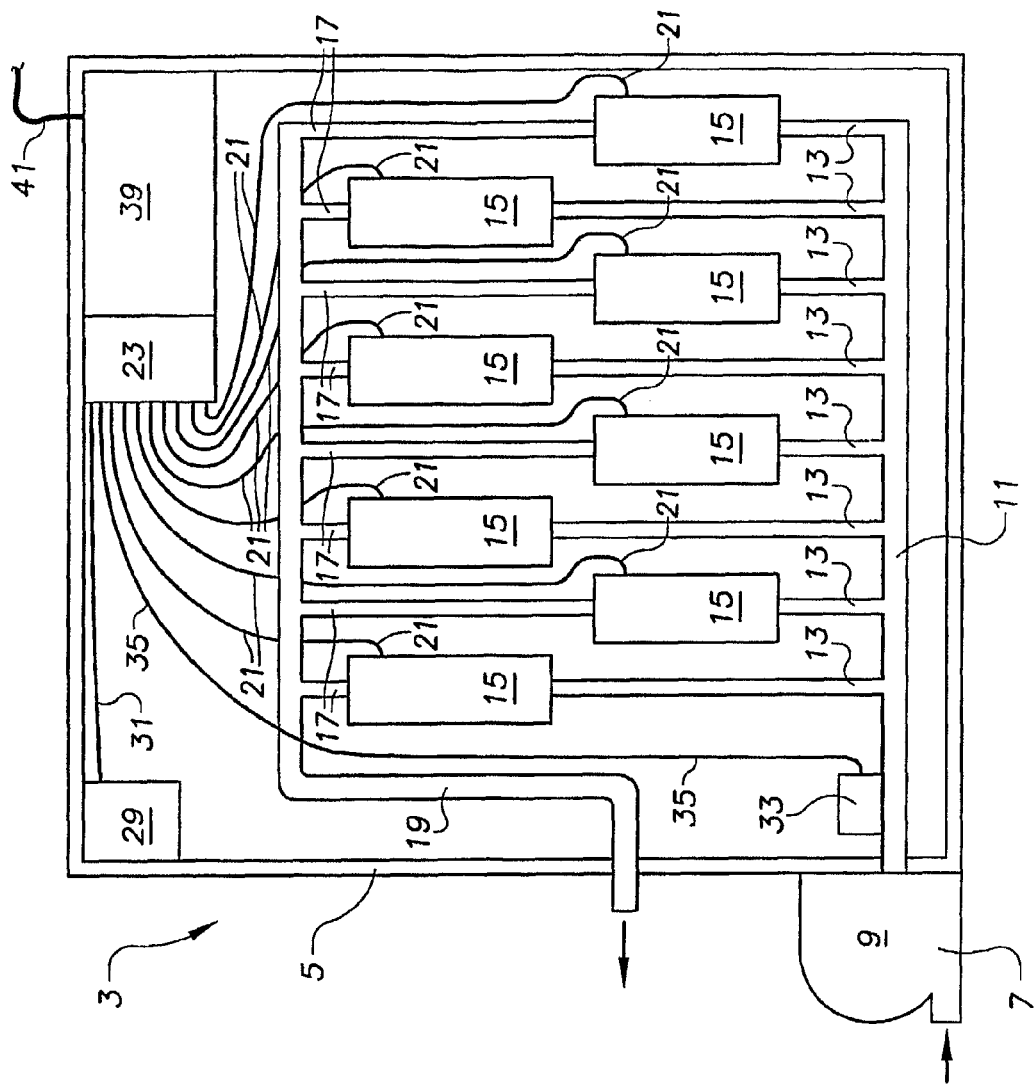
FIG. 1 is a schematic view of a water-monitoring system according to the invention.

As best shown schematically in FIG. 1, the water monitoring system, generally indicated at 3, is preferably placed near a source of the water to be tested and comprises an enclosure 5 with an inlet 7 through which water to be tested is drawn in by a pump 9, which may be inside or outside of the enclosure 5. Inside the enclosure 5, the pump 9 introduces water to be tested to a conduit 11 which supplies this water to a plurality of conduits 13, each of which supply the water to a respective mollusk chamber 15. The water flows through the chambers 15 and then passes to outlet conduits 17, which communicate with outlet pipe 19, which in turn returns the tested water to the water source or deposits it in some other location outside the enclosure 5. The system may be powered by a local power line, generator, or by solar power if feasible for the particular placement of the system.

Each of the chambers 15 contains a mollusk which is exposed to the water flowing through the chamber 15. The behavior of the mollusks in reaction to the water is detected electronically, and, to transmit the individual mollusk data, each of the chambers has an electronic output line 21 connected therewith which connects and transmits electronic signals derived from the position of the shell of the mollusk to analog/digital converter 23.

Vibration and temperature can also affect the behavior of the mollusks, introducing another factor to be considered in addition to toxicants in the water. Consequently, to monitor such influences, the enclosure 5 may be equipped with a vibration sensor 29 which is connected to analog/digital (A/D) converter 23 by connection 31. The temperature and the flow rate of the water may be monitored by a thermometer and/or flow rate sensor 33, connected to the A/D converter by a connection 35.

In the preferred embodiment, the signals from the mollusks and the temperature and other sensor signals are analog signals, and the signals are transmitted to A/D converter 23, which converts the analog signals to digital data and transmits them along one or more lines (not shown), to computer or digital circuitry 39, which may be a computer such as a PC, or a smaller processing system. Preferably, the A/D converter is a component board supported in the housing of computer 39. Where the digital circuit 39 includes a computer, the data received from the A/D converter may be analyzed, and the information derived in the analysis transmitted to a remote location via outside line 41. Such a computer may also generate periodic reports, such as in the alternative arrangement in which a simpler digital circuit is used, the digital circuit 39 may package the data in an appropriate format, such as TCPIP, and transmits it to a remote location by line 41. Line 41 may be a standard analog telephone line, or it may be a more efficient communications method for transmitting the data, such as a digital network, e.g., the Internet, or another telecommunication method, of which there are many well known in the art.

b. Mollusk Chambers

Figure 2:
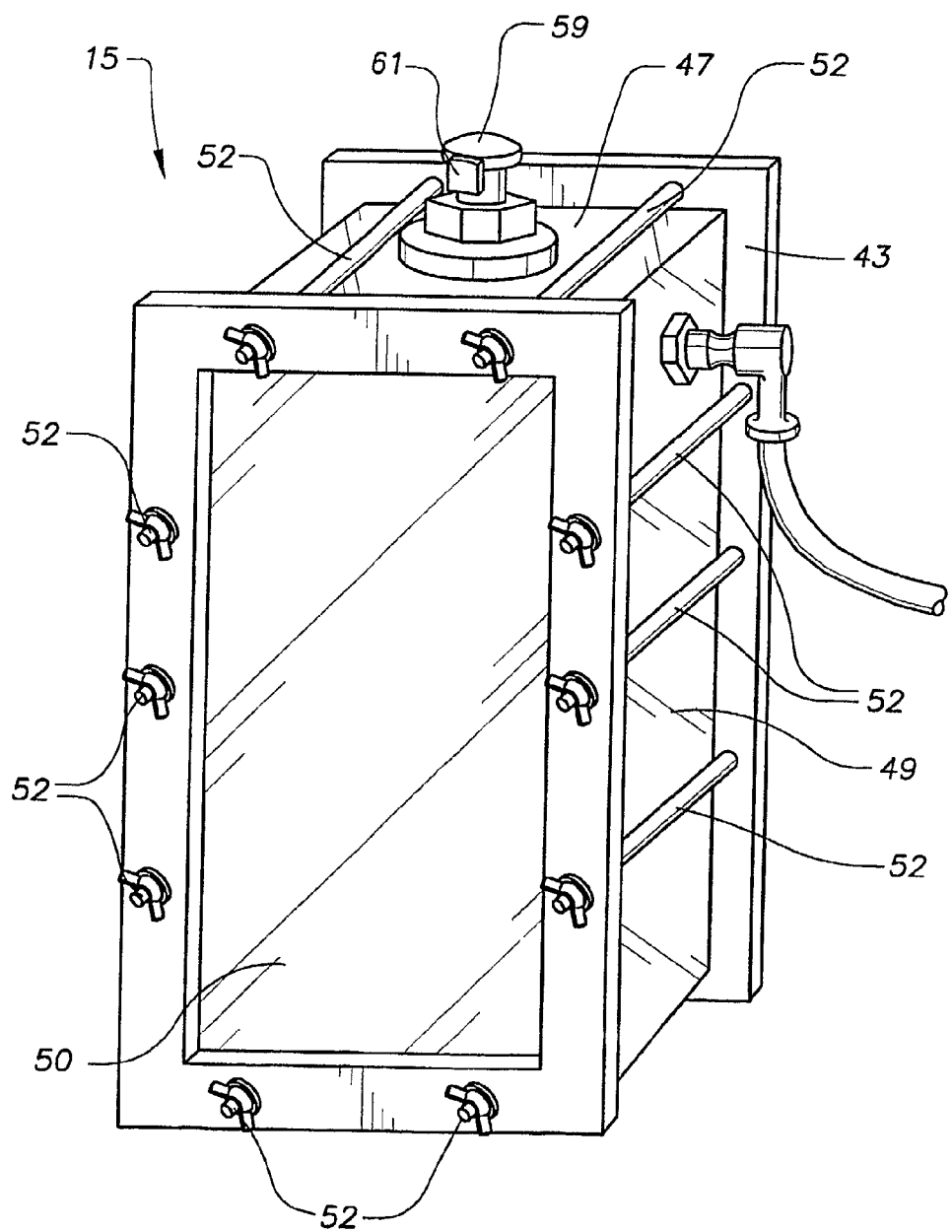
FIG. 2 is a perspective view of one of the mollusk chambers of the system.
Figure 3:
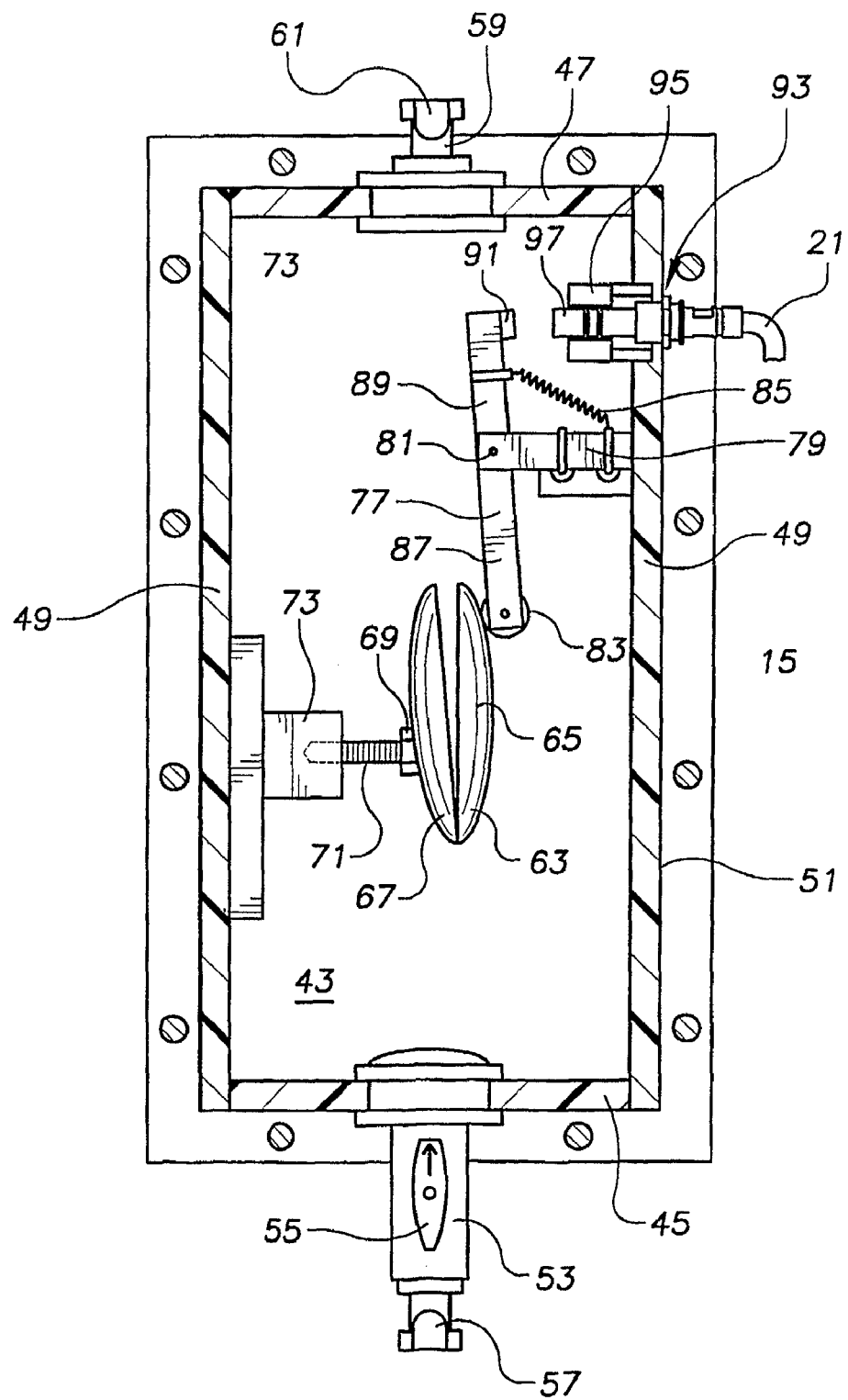
FIG. 3 shows a cross-sectional view through one of the chambers.

In the preferred embodiment, the testing system 3 contains eight chambers 15, substantially identical to each other. FIGS. 2 and 3 show the structure of each chamber 15.

The chamber 15 comprises a back wall 43, a bottom wall 45, a top wall 47 and two laterally spaced, vertically extending side walls 49. A front wall 50 engages the front of side walls 49 and top and bottom walls 45 and 47 to enclose the interior 51 of the chamber 15 in a water-tight manner, such as by securing bolts structure 52 which clamp front wall 50 against the remainder of the chamber 15. A variety of types of securing structures 52 may be used, and it will also be understood that a wide range of structures can be applied to form a water-tight chamber.

The walls of the chamber 15 are preferably formed of clear polycarbonate material. This is especially advantageous because the enclosure 5 contains a light source, preferably a fluorescent light, or one or more LED's adjacent the chamber 15, which keeps the interior of the enclosure 5 uniformly lighted at all times. This continuous lighting prevents diurnal changes in the mollusks, which might otherwise exhibit daily cyclical variations of opening and closing behavior, which would be unrelated to the water quality.

For easy installation and removal of the chambers 15 to the overall system, each of the chambers 15 is a substantially modular unit. To facilitate installation or removal, bottom wall 45 is provided with inlet pipe 53, which includes a valve 55 and a quick-connect fixture 57, which allows it to be readily connected to, or disconnected from, conduit 13 as desired. When connected, the valve 55 is opened, and water from conduit 13 can flow through the inlet 53 into the interior of the chamber 51. Valve 55 is variable in the degree to which it is opened and the flow may thereby be adjusted as desired. Upper wall 47 is similarly provided with an outlet 59 communicating with the interior 51 of the chamber 15, which is also provided with a quick connection 61 to connect to conduit 17. When installed, water flows upward through the chamber 15 from inlet 53, past bivalve mollusk 63, and out of the chamber through outlet 59.

A mollusk, selected for the type of water and the environment of the system, as discussed previously, is mounted inside each chamber 15. Referring to FIG. 3, the mollusk 63, as oriented in the Figure, has a "right" shell 65 and a "left" shell 67. The left shell 67 is glued to a mounting attachment structure in the form of nut 69 which is screwed onto threaded bolt 71. The nut 69 is affixed to the shell 67 at a specific location which is along the lateral center-line of the shell and slightly towards the mollusk's hinge between shell 67 and 65. The threaded bolt 71 is screwed into a mounting structure 73. Depending on the size of the mollusk, the screw structure 71 is screwed to a greater or lesser degree into the mounting structure 73, providing adjustment to position the mollusk 63 approximately in the center of the flow of water through chamber 15, facing upwardly in their naturally observed position.

The presence of toxicants in the water is detected in the system from movements of the mollusk's shell 65 in the chamber 15. A sensing device generally indicated at 75 monitors the movements of the shell of the mollusk. The sensing device 75 has a lever 77 which is pivotally supported on a mounting structure 79 affixed to side wall 49. The lever 77 pivots about pin 81 and has a roller 83 mounted on a first portion 87 of the lever 77 which extends downward from the pivot point 81 and rests against a front portion of the mollusk at approximately its lateral center line. A spring 85 connects one side of the lever with the mounting structure 79 and biases the lever 77 to rotate so that the roller 83 is in engagement with the shell 65 of the mollusk 63 at all times. The spring 85 is of a strength sufficient to keep the roller 83 engaged with the shell 65, but weak enough so that it has no effect on the activity of the mollusk in opening and closing its shell. In the preferred embodiment, the spring constant of the spring 85 is preferably in the range about 0.1 to 0.4 pounds per inch, and most preferably in the range of 0.16 to 0.3 pounds per inch.

The lever 77 also includes an upper portion 89 which extends upwardly from the pivot point 81 and supports a magnet 91 thereon. The ratio of the distance from roller 83 to the pivot point 81 relative to the distance from the magnet 91 to the pivot point 81 is generally in the range of 1:1 to 1:2.

Figure 4:
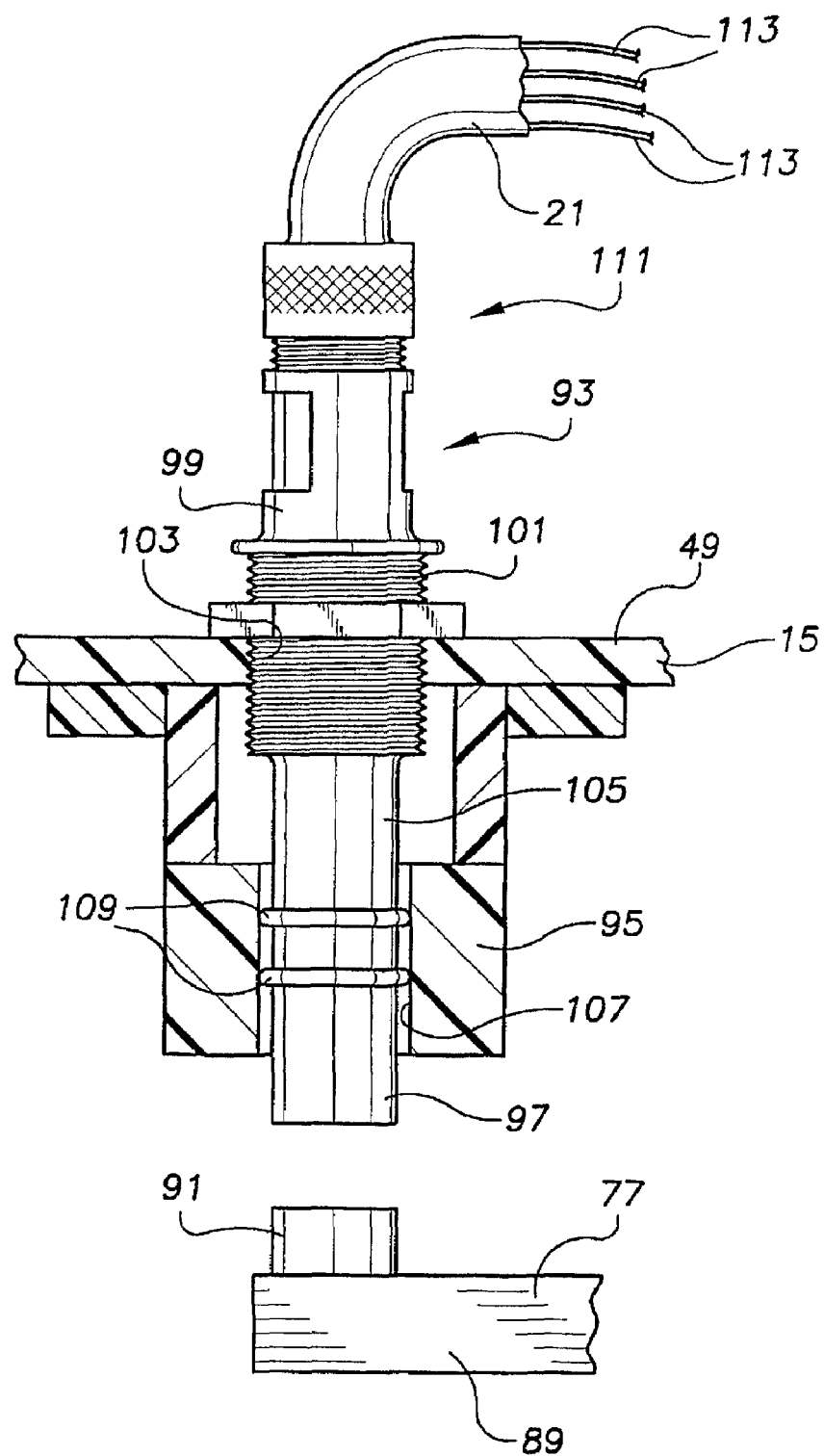
FIG. 4 is an enlarged detail view of the Hall effect sensor shown in FIG. 3.

As best shown in FIG. 4, the sensor structure 93 preferably comprises a Hall effect sensor 99 which has a sensor head 97 projecting through tube 95 affixed to wall 49 into the interior 51 of the chamber 15. Any suitable sensor may be used in the system, but particularly preferred is a Hall effect sensor produced by Xensor Corporation of Pittsburgh, Pa. Similarly, any magnet may be used, but in the preferred embodiment the magnet is the AlNiC magnet sold by the Duramagnet Co. As the mollusk 63 opens and closes its shell, the movement causes pivoting of the lever 77 about pivot 81, which also moves magnet 91 on the end of lever portion 89 toward or away from the Hall effect sensor 99, and the output of the Hall effect sensor varies as the magnet 91 moves toward and away from the sensor 97 with movement of the shell 65 of the mollusk 63. The sensor 99 includes a threaded portion 101 which is threadingly received into a threaded aperture 103 in wall 49. The precise position of the head 97 within the chamber 15 is adjusted by screwing the sensor 99 to the proper location in threaded aperture 103 during installation of the mussel 63 in the chamber 15.

Since water flows continuously through the chamber 15, and the sensor 99 extends through aperture 103 in chamber wall 49, precautions are taken against leakage. The sensor 99 includes a cylindrical portion 105 which supports the head 97 and extends through a cylindrical aperture 107 in the sensor support structure 95. This passage 107 through support structure 95 is sealed against leakage by two or more O-rings 109, which sealingly engage the sides of the passage 107 and prevent water from leaking out through the sensor structure 93.

The output of the sensor 99 is electronic analog signals. The outward end of the sensor 99, generally indicated at 111, is connected with cable 21, which comprises three separate wires 113 which each connect with the Hall sensor. One wire carries in-voltage ($V_{in}$) (preferably 5 volts), a second wire connects to ground, and a third wire carries the out-voltage ($V_{out}$), which is the analog data representing the distance to which the mollusk shell is opened, which distance is referred to herein as "the gape" of the mollusk.

The A/D converter 23 communicates with the sensor 99, along lines 113, and preferably interrogates the sensor at a frequency of 2 Hz, i.e., once every ½ second. The analog output of the sensor 99 is converted to digital form and logged to a disk drive in computer 39, or to a remote location, preferably about once every minute. Alternatively, computer 39 may calculate Degree of Alarm ("DOA") in a running real-time application.

Figure 5:
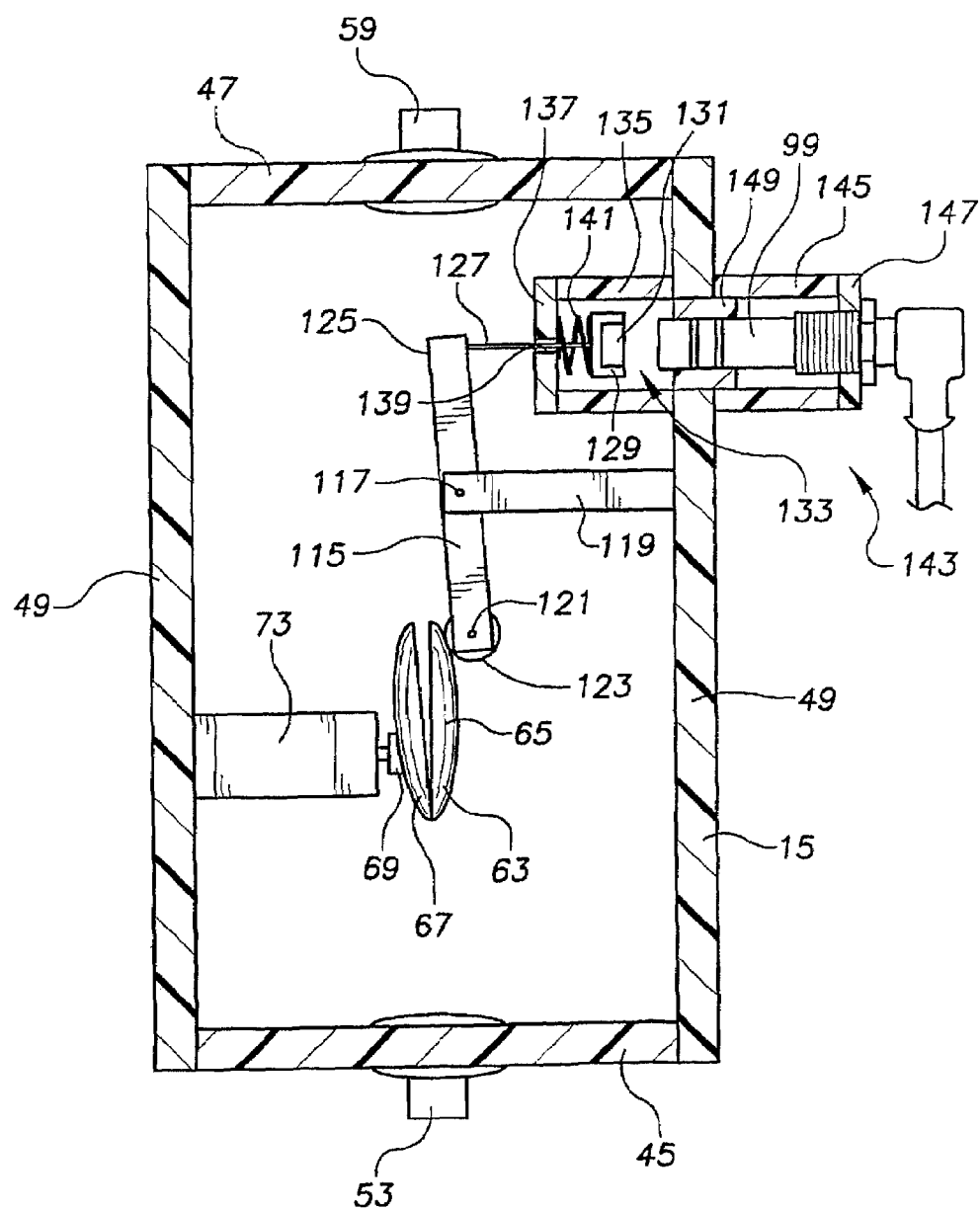
FIG. 5 shows a cross-sectional view as in FIG. 3 of an alternate embodiment of the chamber.

FIG. 5 shows an alternate embodiment wherein the chamber 15 is provided with a similar mounting and support structure for mollusk 63, but a different sensor structure. This alternate design is particularly desirable where sediment from the water is likely to form in the system. Lever 115 is pivotally supported about pin 117 on support structure 119. One end 121 of the lever 115 supports the pivotally mounted roller 123 which engages the shell 65 of the mollusk. The other end 125 of the lever 115 is connected by a stainless steel wire 127 to a nylon housing 129 which holds magnet 131. The magnet is supported inside a chamber generally indicated at 133 which is formed by a cylindrical member 135 attached to side wall 49 and an inside member 137 attached to the inward end thereof. This member 137 has an aperture 139 therein through which the wire 127 extends and connects to the magnet housing 129. This aperture is fairly small, permitting passage of water as may be necessary, but limited in terms of the amount of material that can pass therethrough, limiting the possibility of contamination or accretion of material on the magnet 131 which might arise due to sedimentation from the water in chamber 15 and affect readings from the sensor 99.

A bias means in the form of spring 141 is provided between end wall 139 and the back of the nylon container 129 for magnet 131. This biasing structure 141 urges the magnet outwardly towards side wall 49 and creates tension in wire 127 which rotates lever 115 so that the roller 123 rides on the shell of the mollusk, and travels therewith. Hall effect sensor 99 is in this embodiment supported in a structure generally indicated at 143 which provides for adjustment of the placement of sensor 99. This structure comprises a cylinder 145 and an outer wall 147 supported on the outward side of side wall 49. An inner cylinder 149 receives the sensor end of sensor 99 therethrough in a sealing fashion with O-rings surrounding the sensor end, in a fashion similar to that described with regard to the preferred embodiment.

For adjustment purposes, the outer wall 147 is threaded to allow adjusting movement of the sensor 99 in and out of structure 143. The outer end of the sensor 99 is connected to the system as in the preferred embodiment, by a cable and a connector.

When the mollusk in this embodiment moves the shell 65, it causes the lever 115 to rotate and move with the magnet structure 131. This moves the magnet into proximity with, or away from, the Hall effect sensor, which causes the sensor to produce an output related to the position of the shell. The walls of the tubular structure 135 are of a teflon material to prevent friction with the nylon structure 129 surrounding the magnet 131, and to ensure the smooth reciprocating movement of the magnet in the apparatus.

c. Physical Installation of Mollusks in the System

The present system is particularly advantageous from the standpoint of facilitating installation or replacement of the mollusks or the chambers 15.

Figure 6:
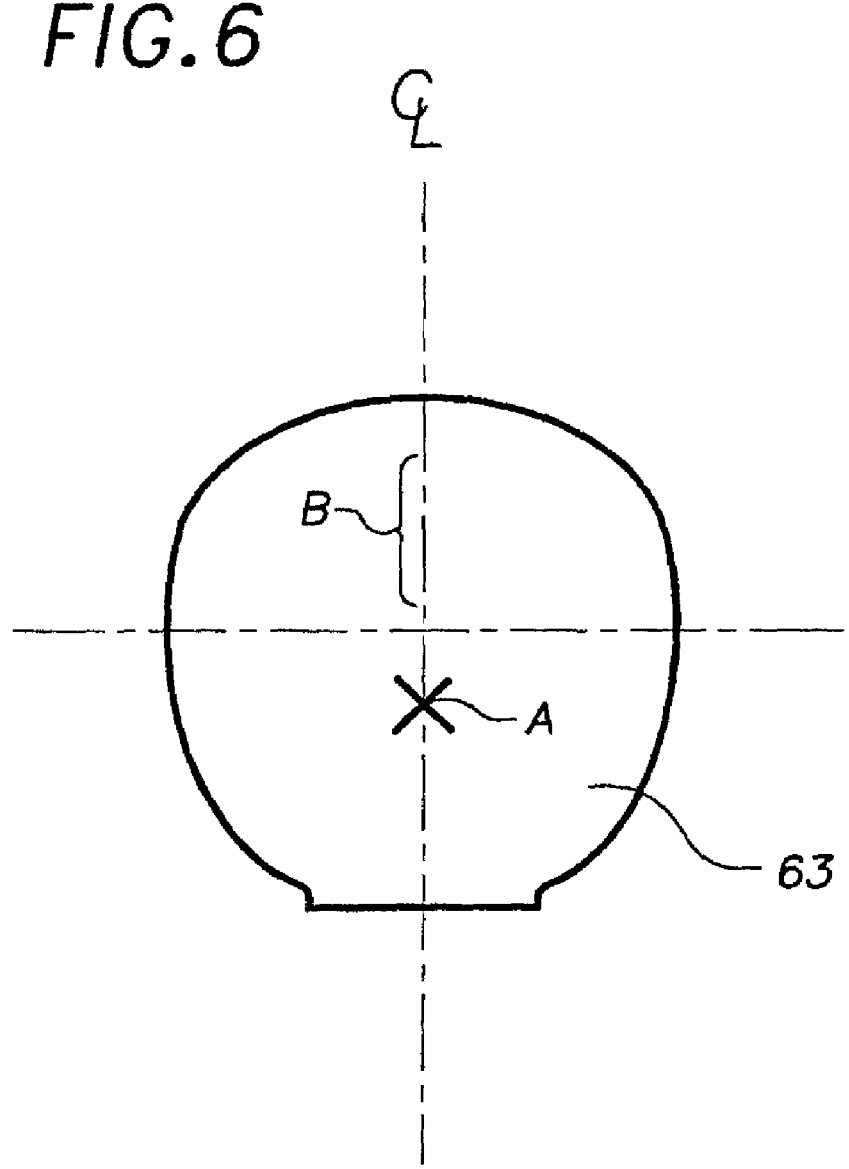
FIG. 6 is a schematic view of the points of engagement of the apparatus with a mollusk in the chamber.

The mollusk is mounted in the chamber 15 by first mounting an attachment structure, such as nut 69, on the left shell of the mollusk. The attachment structure is preferably glued to the shell, and is positioned thereon using a jig. The jig positions the structure on the shell along the lateral center line of the mollusk and about one-third of the lengthwise dimension of the mollusk from the hinge of the shell, i.e., closer to the hinge than to the opposing open end of the shell, as is best indicated in FIG. 6, wherein an optimal placement position for the attachment structure is indicated by reference character A.

A mollusk is then transported in any convenient container to the system 3 installation. The chamber 15 to be used may be transported at the same time, empty of water because the mollusk is not yet installed. Alternatively, the chamber 15 may already be in the system 3, in which case it is removed therefrom by releasing the quick-connects 57 and 61. The front panel of the chamber 15 is then opened to access the interior of the chamber 15.

The mollusk is attached via the attachment structure 69 to an adjustment structure such as threaded element 71. After the mollusk is so attached, the threaded element 71 is secured in support structure 73 on the wall of the chamber 15. The threaded element 71 is screwed into the support structure 73 to a point at which the mussel is in the lateral center line of the chamber 15, in the middle of the flow of water through the chamber, and facing upward away from the inlet 57.

Alternatively, the threaded element 71 may be first screwed into mounting structure 73, and nut 69 is then connected therewith. Other assemblies for mounting a mollusk can be envisioned, the benefits of the present invention being found, inter alia, in the securement of an attachment structure to the shell, especially using a positioning yoke, and by connecting the attachment structure to a support in a way that allows adjustment of the position of the mollusk.

After mounting of the mollusk, the sensor system 75 is allowed to engage the mollusk shell, with roller 83 biased to rest against the shell by spring 85. The lever 77 is supported in the chamber 15 in a fixed location, but its dimensions are such that roller 83 contacts the upper shell of the mollusk at a middle area along the center line of the mollusk 63, generally indicated at B in FIG. 6.

d. Calibration

A major advantage of a sensor system having a movable member such as lever 77 is that it keeps the magnet and sensor 99 in appropriate vertical and lateral alignment with each other while allowing for variations in the size of the mollusk. The thickness of the mollusk, however, may result in some variation in the distance of the magnet on lever 77 from the Hall effect sensor head and this necessitates some initial calibration of the device where the mollusk is closed.

This calibration is performed during installation by clamping the mollusk closed, and then adjusting the position of sensor 77 by rotation thereof in threaded aperture 103. This adjustment is performed with electrical contacts connected to the sensor 99 until the output voltage $V_{out}$ is in the range of 1.2 to 1.4 volts. Once this adjustment is completed, the mollusk shell is unclamped, and the chamber 15 may be installed in the system 3 and filled with water from the associated conduit 13.

Generally, the mollusk gape will vary from about zero in the closed position to about 1 to 1.5 cm in the open position. In the preferred embodiment, as the mollusk opens its shell, the magnet moves farther away and the sensor output voltage $V_{out}$ increases. Additional adjustments of the sensor are made if necessary to maintain this output voltage $V_{out}$ within a desired range. Preferably the $V_{out}$ of the Hall effect sensor ranges from 1.2 to 1.4 volts when the mollusk is closed to 1.9 to 2.5 volts when the mollusk has its shell open at its maximum normal gape. If the output voltage increases to 3 volts or more, this normally indicates that the gape of the mollusk has become completely wide open, and that the mollusk is dead or under the effect of a muscle-relaxing toxicant.

Further calibration of the system is performed after one or more mollusk chambers are properly installed. The digital circuitry or computer 39 then monitors the gape of the mollusk during approximately the first three days after installation. From the gape values derived during this period, the computer derives a natural maximum gape value for the individual mollusk. Subsequent calculations based on output from the mollusk chamber 15 are based on the percentage of gape, i.e., the percentage of the maximum gape output value that the presently detected gape output value represents.

e. Detection of Toxicants

When the system 3 contains a number of mollusk chambers 15, the individual mollusk percentage gape data for all of the mollusks of the system is totaled, and the average percentage gape value calculated periodically per sampling interval by computer 38. This mean data value $G_i$ is the variable used as the mollusk output data for determining if toxicants are present in the water being screened.

In the present specification, $G_i$ means the current average mollusk gape data, $G_{i-1}$ means the most recent earlier mollusk output value, $G_{i-2}$ the next earlier mollusk output variable, etc. The oldest of the gape values is $G_{i-n+1}$. Preferably, the set of data values $G_{i-n+1}$ to $G_i$ are stored in a FIFO (first-in, first-out) stack data structure in the computer doing the analysis. The stack acts as a shift register, shifting earlier data values as the new data value $G_i$ is acquired. Preferably the value of n is 30, and the data values G are acquired every half-second.

A variable referred to as Degree of Alarm ("DOA") is derived from the mean mollusk output data using one of a variety of analysis formulae or methods, ranging from simpler models to more complex systems based on neural net technology that can identify the particular toxicant types that are present in the water and causing a reaction by the mollusks.

DOA is preferably a number greater than zero, with higher numbers indicating presence of toxicant. When the calculated DOA value exceeds a predetermined threshold, an alarm condition may be triggered, setting off whatever notices and communications are desired to react to a potential toxicity detection. These communications may include transmitting a fax, activating a pager, sending an automatic telephone message, alerting an Internet browser of an operator, updating a web site, or any other appropriate notification method. In addition, a sample of the water being tested is automatically extracted by the system 3 by an auto sampler and stored at about 4° C. for laboratory analysis.

The threshold DOA value will vary depending on the particular installation. For example, where drinking water is being screened, the DOA threshold value should be low so as to trigger an alarm with greater sensitivity. On the other hand, where a water source such as a river that is already environmentally compromised is being tested, a high DOA may be more appropriate.

When the toxicant in the water is of a type which causes relaxation of the mollusk, the gape will exceed the normal maximum gape for a substantial period of time, e.g., for several minutes. This condition will trigger an alarm condition which may be identified by the output of a high DOA value.

Similarly, if the toxicant in the water arrives in such a high concentration that it kills the mollusk, the mollusk shell will open to a very wide gape, possibly as much as 200 or 300% of the normal maximum gape. This very high gape value will be interpreted to indicate death of the mollusk, and notification of this will be sent out through the communications line to alert an operator. Where several mollusks in the system die contemporaneously, it is reported as a toxic event. This report may be either by a communication different from DOA representing a major lethal event, or by a high DOA value.

In more usual toxic events, the concentration of the toxicant rises slowly, and the mollusk reacts by closing its shell above a certain concentration. It has been noted, however, that prior to closing its shell (i.e., gape=0), the mollusk will initially start a pumping action, meaning an initial agitation.

One aspect of the invention is to detect the initial "pumping" of the mollusk when concentration of toxicant is still low. This pumping is accomplished by a limited opening and closing of the shell in a fluttering action. In terms of data output for the sensor, there is a great deal of variation in the percentage gape values during the pumping period indicative of increased movement of the shell. For analyzing the degree of movement of the mollusk shell, a movement value indicating degree of opening and closing activity of the mollusk is calculated which can be compared to a threshold value above which, the movement of the shell indicates the pumping action.

According to an aspect of the invention, the variance over time of the gape values is one of the best statistical indicators of the pumping of the mollusk. By the term variance, what is meant is a determination of the variability of the gape values from a mean value, which may be determined or expressed using a variety of functions. Particularly preferred, however, is the classical calculation of variance as:

$$V = \sum_{j=1}^{n}(G_{i-j+1} - M)^2$$

where M is the mean (i.e., average) value of the gape values $(G_{i-n+1}, \ldots G_i)$.

A number of methods or systems can be employed to reliably detect toxicants based on the mollusk output data. The methods of determining DOA may also use other pertinent statistical values derived from the gape values. These statistical values include:

the first derivative G' of the data values, preferably calculated as $$G_i' = G_i - G_{i-1};$$

the second derivative G" of the data values, preferably calculated as $$G_i'' = G_i + G_{i-2} - 2(G_{i-1});$$

and the traveling mean value M, preferably calculated as $$M = \frac{1}{n}\sum_{j=1}^{n}(G_{i-j+1}).$$

The following examples detail particularly preferred methods for determining DOA.

EXAMPLE 1

In a basic method for toxicant detection, DOA is calculated continuously using the formula $$DOA = (V \cdot |R|)/M$$

wherein V is the mean variance in gape over a recent period of time, preferably 30 seconds, R is the mean regression of the gape over the period (regression herein meaning the slope of the best-fit line through the data values of the time period). M may be the traveling mean as defined above, or may be the mean gape taken over another longer period, preferably about one hour.

Figure 7:
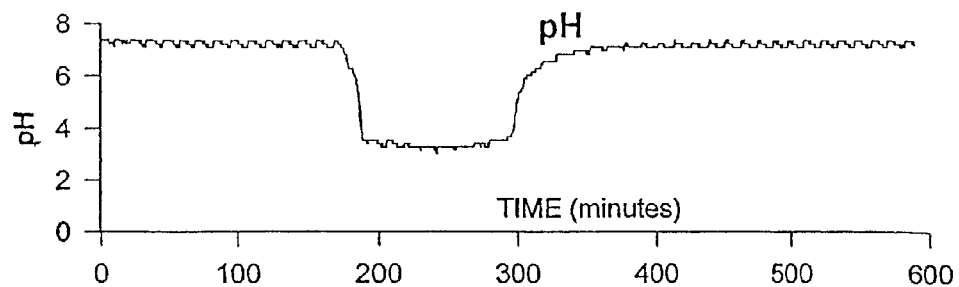
FIGS. 7 through 10 are graphs illustrating application of a toxicant detection method of the invention to a test exposure to sulfuric acid.

An implementation of this method is shown by the graphs of FIGS. 7 to 10. Water being screened by a system as described previously was loaded with sulphuric acid, resulting in a drop in pH as shown in the graph of FIG. 7.

Figure 8:
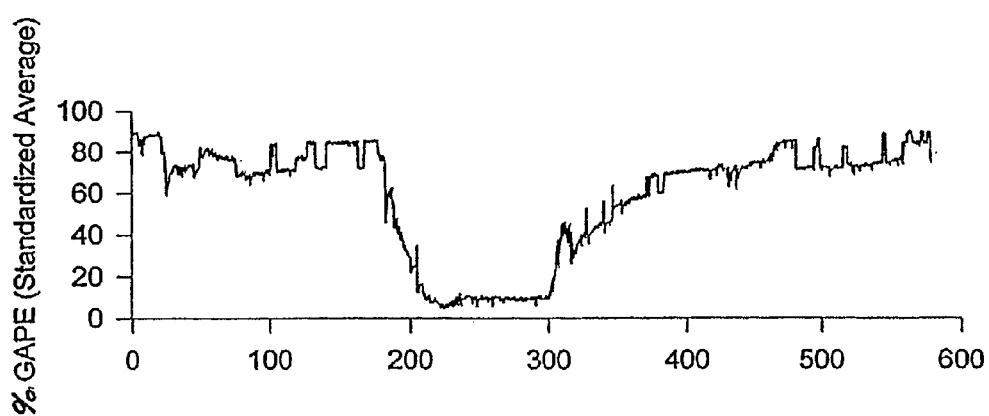

The average percentage gape of the mollusks exposed to the water is shown in FIG. 8, wherein it can be seen that just prior to the 200 minutes mark, mollusks began to reduce their gape, dropping the gape to less than about 10% of the normal maximum shortly after 200 minutes.

Figure 9:
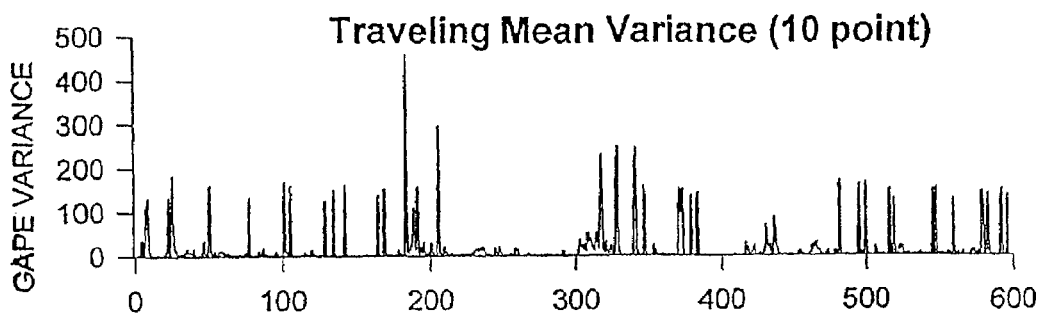
Figure 10:
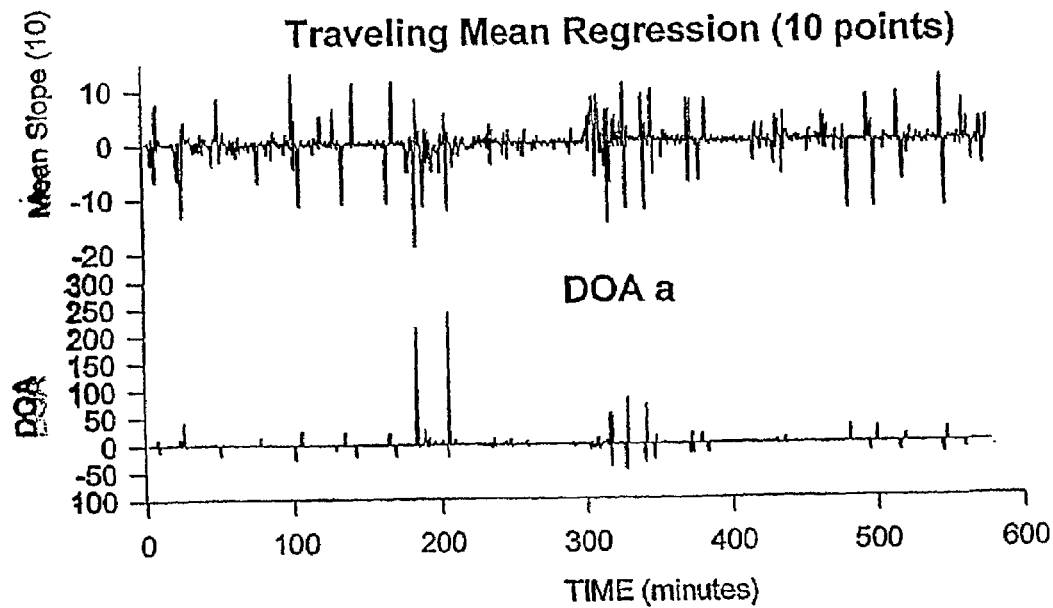

FIG. 9 shows the mean variance taken over a FIFO set of the ten most recent values. It can be seen that variance spikes shortly before 200 minutes, while percentage gape is still as large as 40%. Traveling mean regression of the last ten data values is shown in FIG. 10 above the ultimate DOA values calculated. A spike in DOA values, greater than 100 or 150 indicating toxicity, appears before 200 minutes.

EXAMPLE 2

The variance value may also be used to select which method or function is to be used to interpret the mollusk data and calculate DOA. In such a system, the variance is calculated and compared with a pre-selected threshold value.

When the variance is below this threshold value, a first, less sensitive function of the gape data values is used to calculate the DOA value. Such a function might be a linear calculation such as $$DOA = (1-G_i)*10$$

which would yield a DOA value between 0 and 10, with 10 corresponding to the mollusk completely closing its shell and strongly indicating presence of toxicant. Also, particularly preferred for such functions are Logistic or Gaussian (or sigmoid) functions as illustrated in FIG. 11, which may be modified to keep DOA values in range, and also to provide sensitivity in specific sub-ranges.

Figure 11:
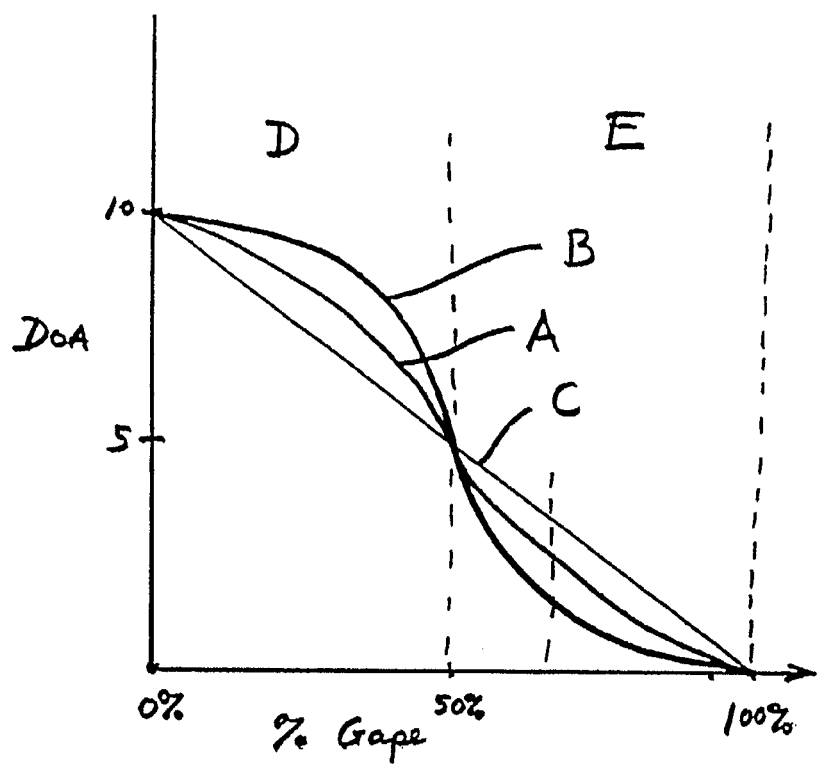
FIG. 11 is a graph illustrating various functions which may be used to determine Degree Of Alarm from mollusk behavior.

As shown in FIG. 11, both the Logistic function A and the Gaussian function B have a central region in the area of 50% gape wherein a change in gape has a more pronounced effect (a steeper slope or differential) than in a straight linear relationship C. In areas near 100% gape and 0% gape, the slope or differential of the curve is not as steep as in the middle region. The result of the shapes of the Gaussian or logistic curves is that where gape is greater than 50%, in region D, the possibility of false negatives is reduced, while when gape is less than 50%, in region E, the possibility of false positives is reduced. Depending on the particular system placement or types of mollusks, the curves may be deformed so that the intersection with the linear function C is at a point greater or less than 50%. Other functions may also be used, a primary concern being that the function be in a negative monotone with respect to increasing gape.

When the variance value is greater than or equal to the threshold value, the DOA value may be calculated by a different function which amplifies the calculation from the closing of the shell during the period of high variance. Particularly preferred is a more sensitive high-variance function:

$$DOA = f(G_i) + V/K$$

Wherein $f(G_i)$ is a linear, Logistic, or Gaussian function, or a-combination thereof, V is the variance of the set of stack values, and K is a preselected sensitivity constant selected based on the desired degree of sensitivity of the system.

EXAMPLE 3

Figure 12:
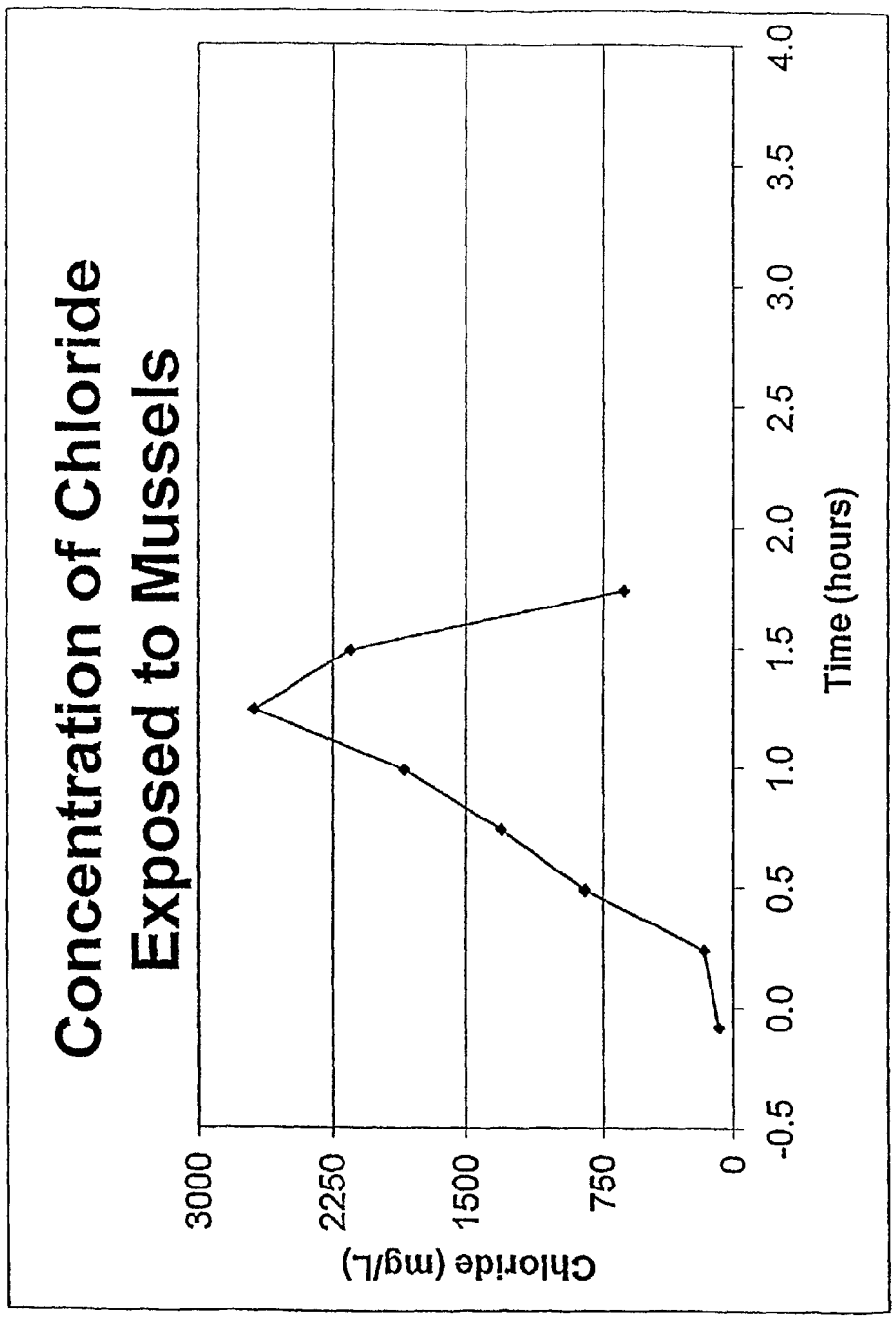
FIGS. 12 to 16 are graphs illustrating results of a toxicant detection method of the invention in reaction to a presence of chloride in the water.
Figure 13:
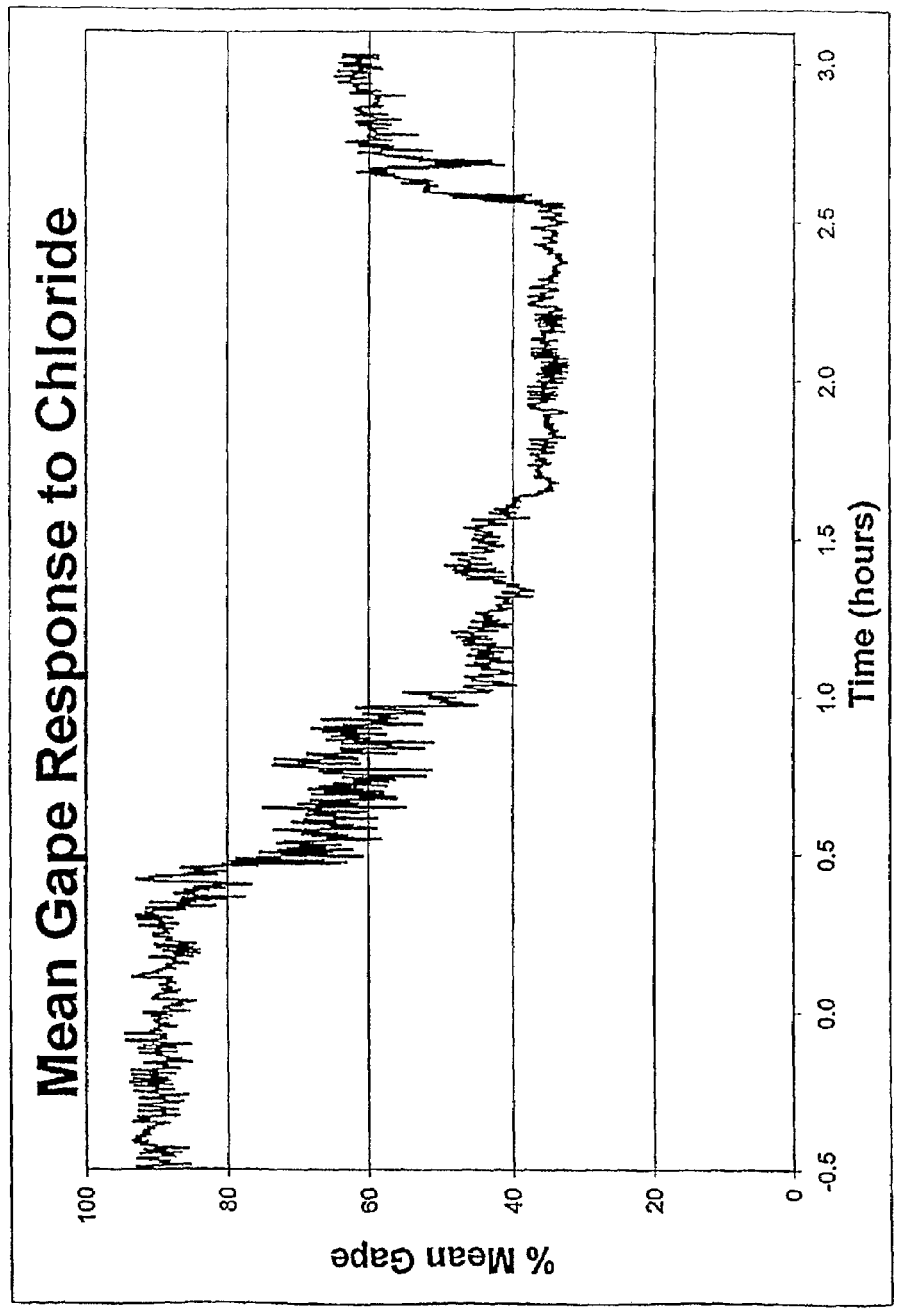
Figure 14:
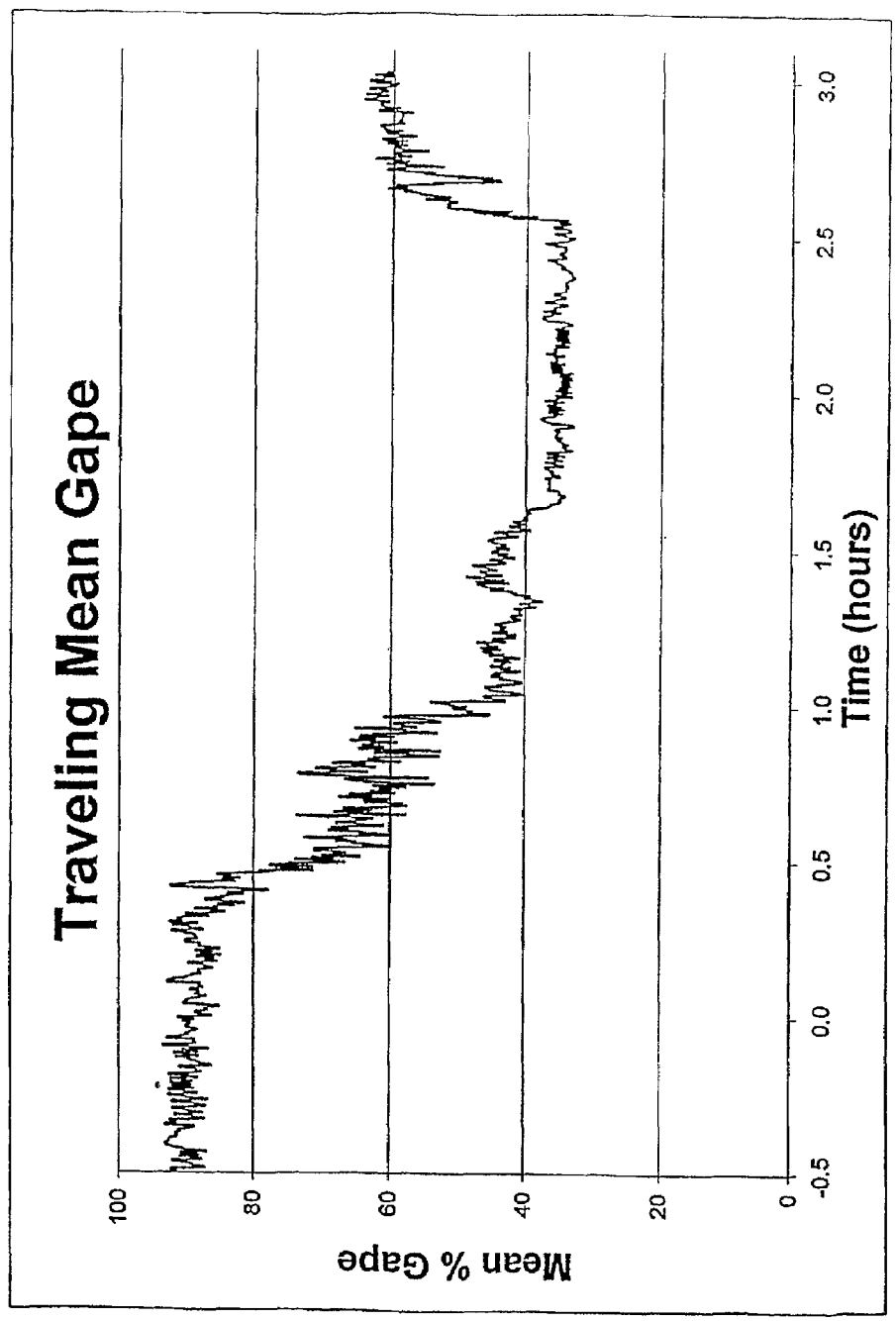

An implementation of such a DOA method using a Logistic calculation, with a variance factor added for variances over 50, is illustrated by the graphs of FIGS. 12 to 16. As seen in FIG. 12, water being screened was loaded with a gradually increasing concentration of chloride (as aqueous NaCl). The raw gape data shown in FIG. 13 exhibited decreasing gape over time to less than 40% of normal maximum gape. This data was smoothed, as seen in FIG. 14, by calculation of the traveling mean over the set of stack values.

Figure 15:
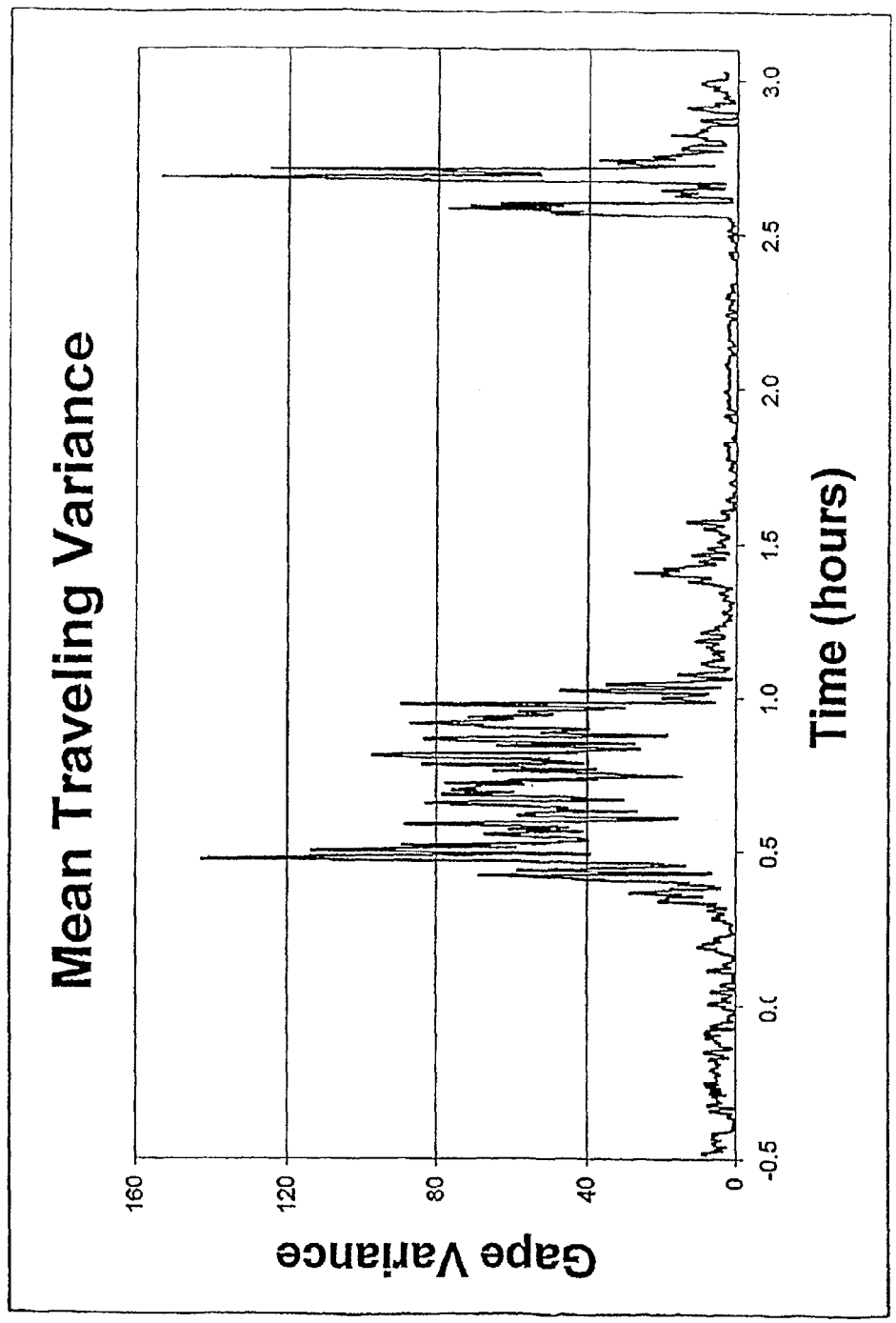
Figure 16:
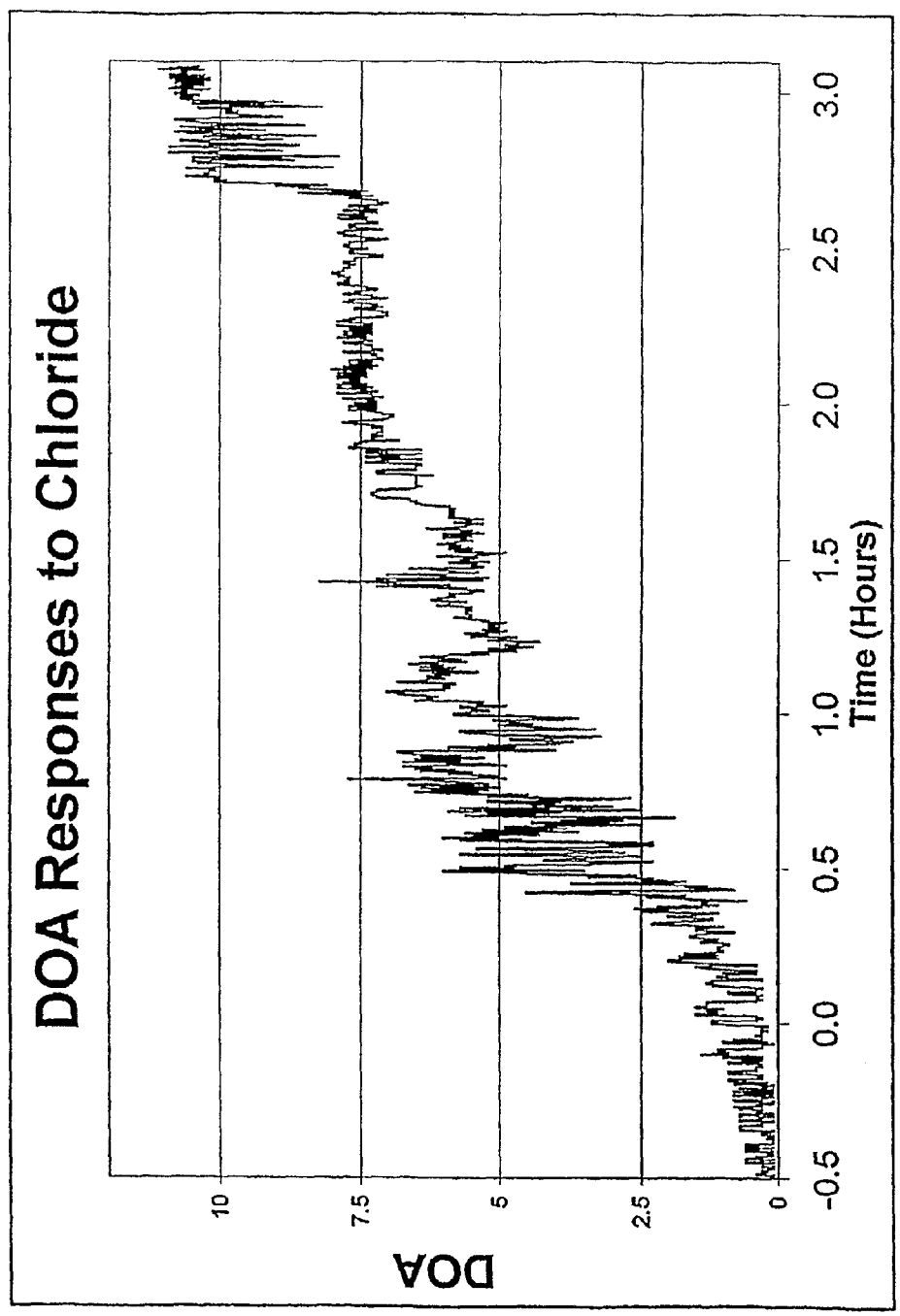

As best seen in FIG. 15, variance of the gape values indicates substantial mollusk activity between 0.5 and 1.0 hours. This resulted in a DOA output as seen in FIG. 16, already yielding a DOA greater than 5 at 0.5 hours, while chloride concentration was still relatively low.

EXAMPLE 4

Figure 17:
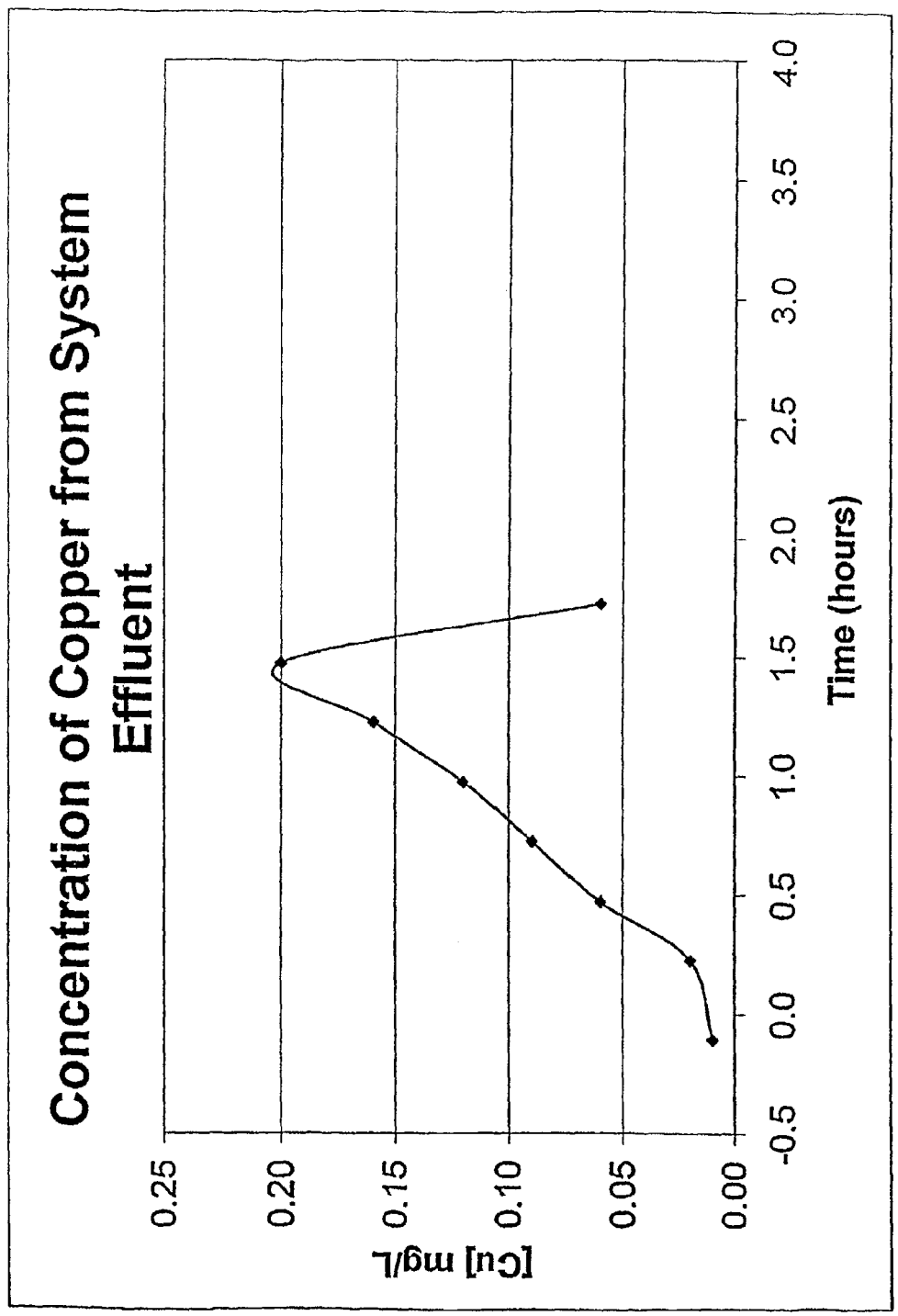
FIGS. 17 to 21 are graphs illustrating results of a method as in FIGS. 12 to 16, but in reaction to a presence of copper in the water.
Figure 18:
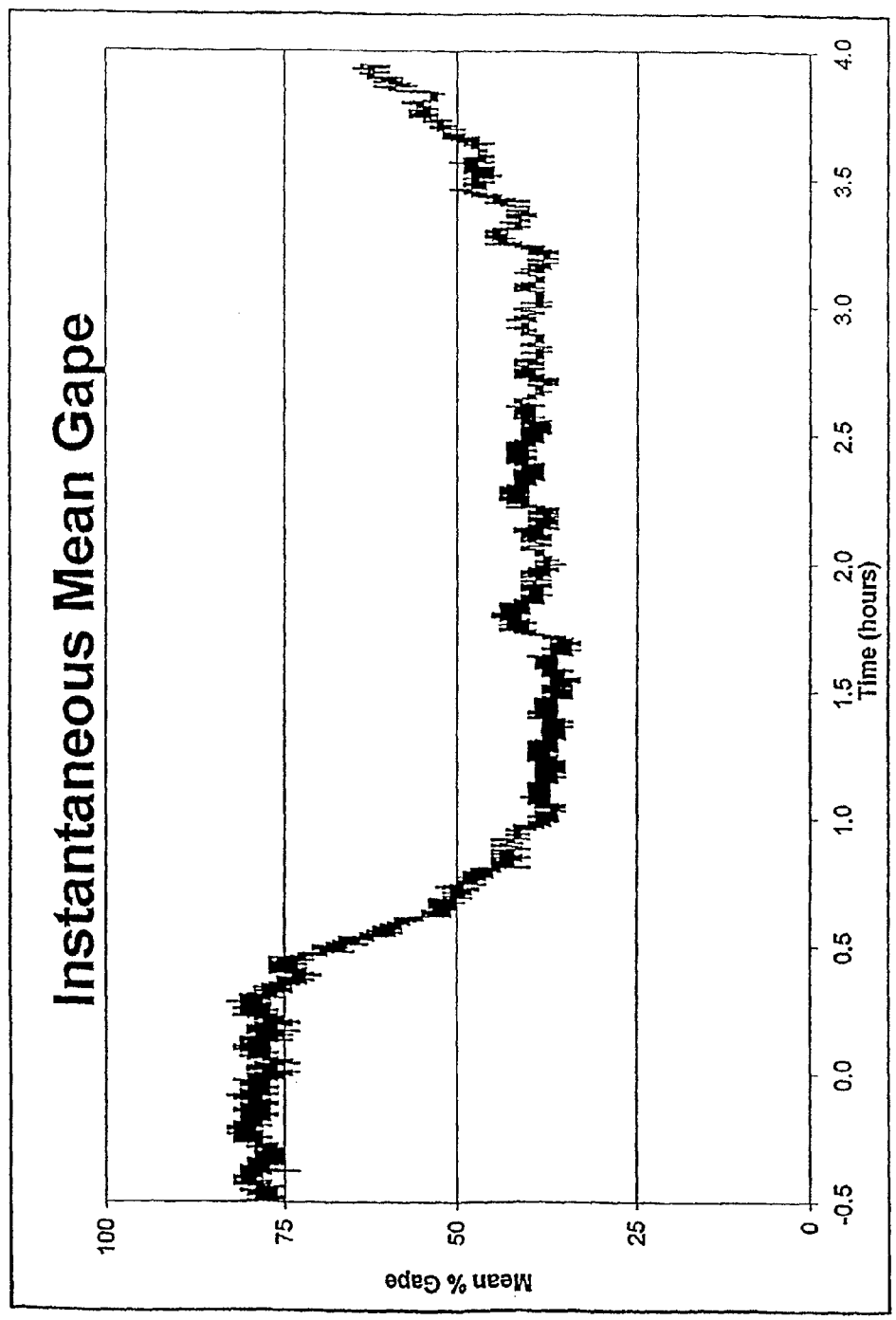
Figure 19:
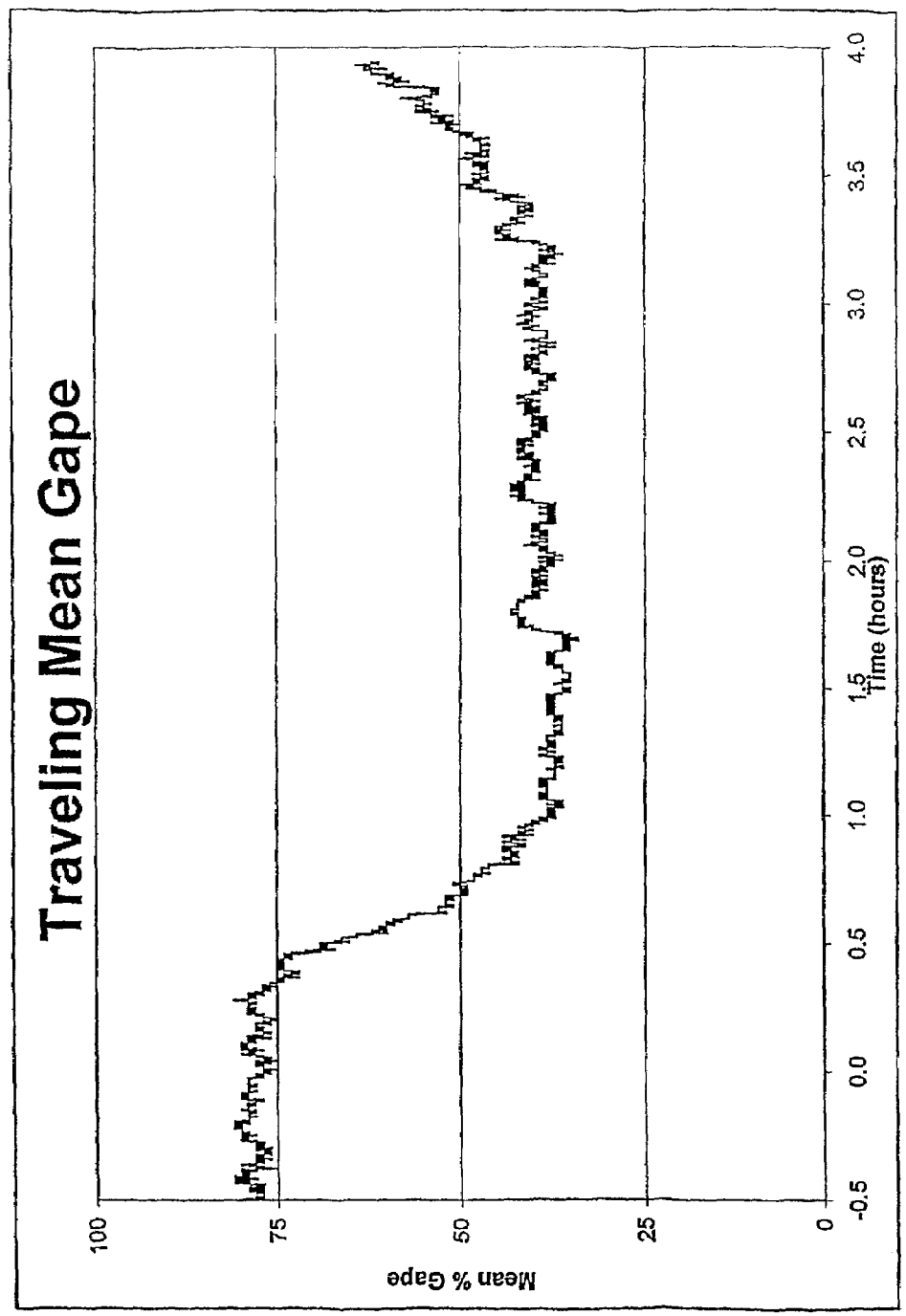
Figure 20:
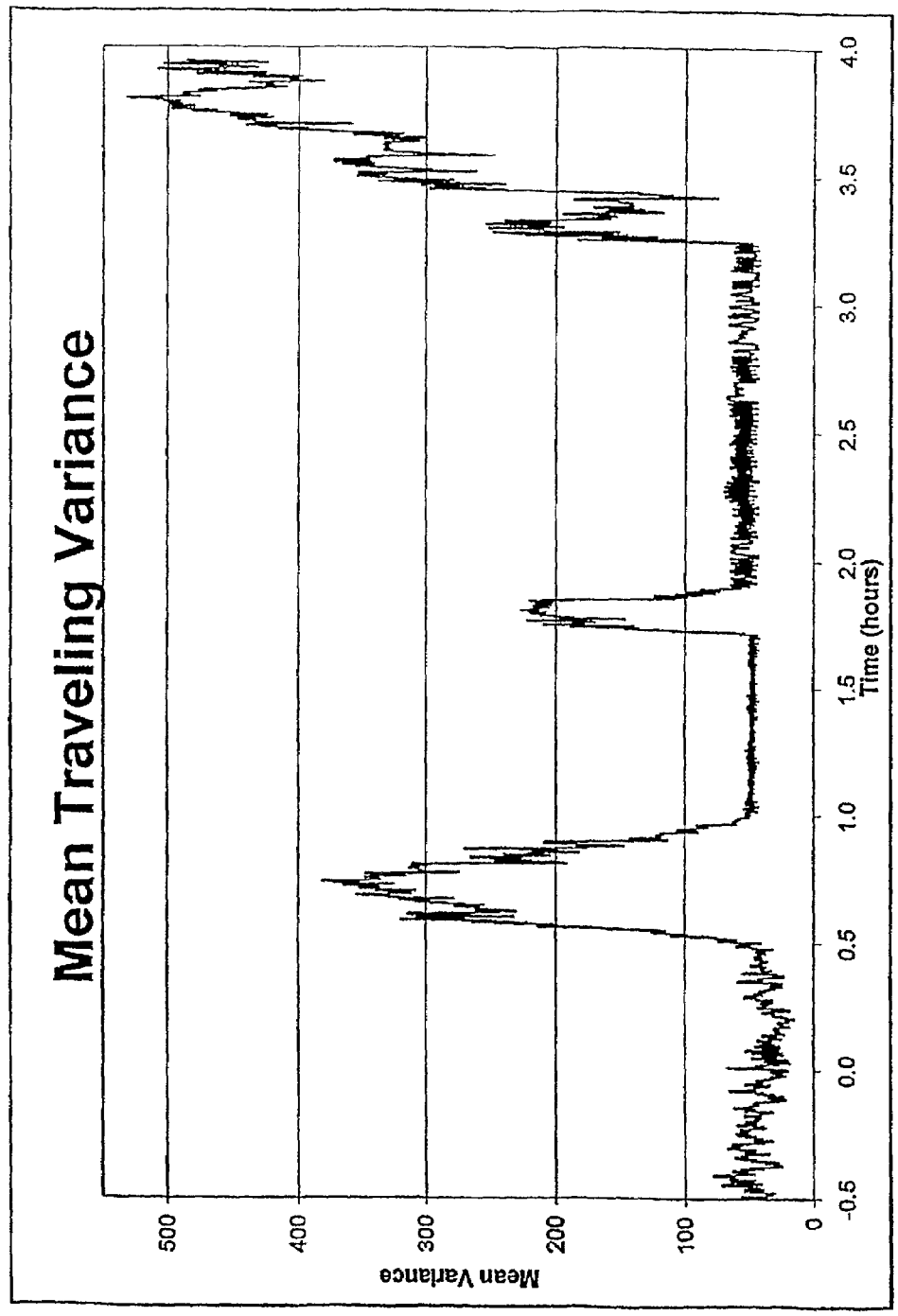
Figure 21:
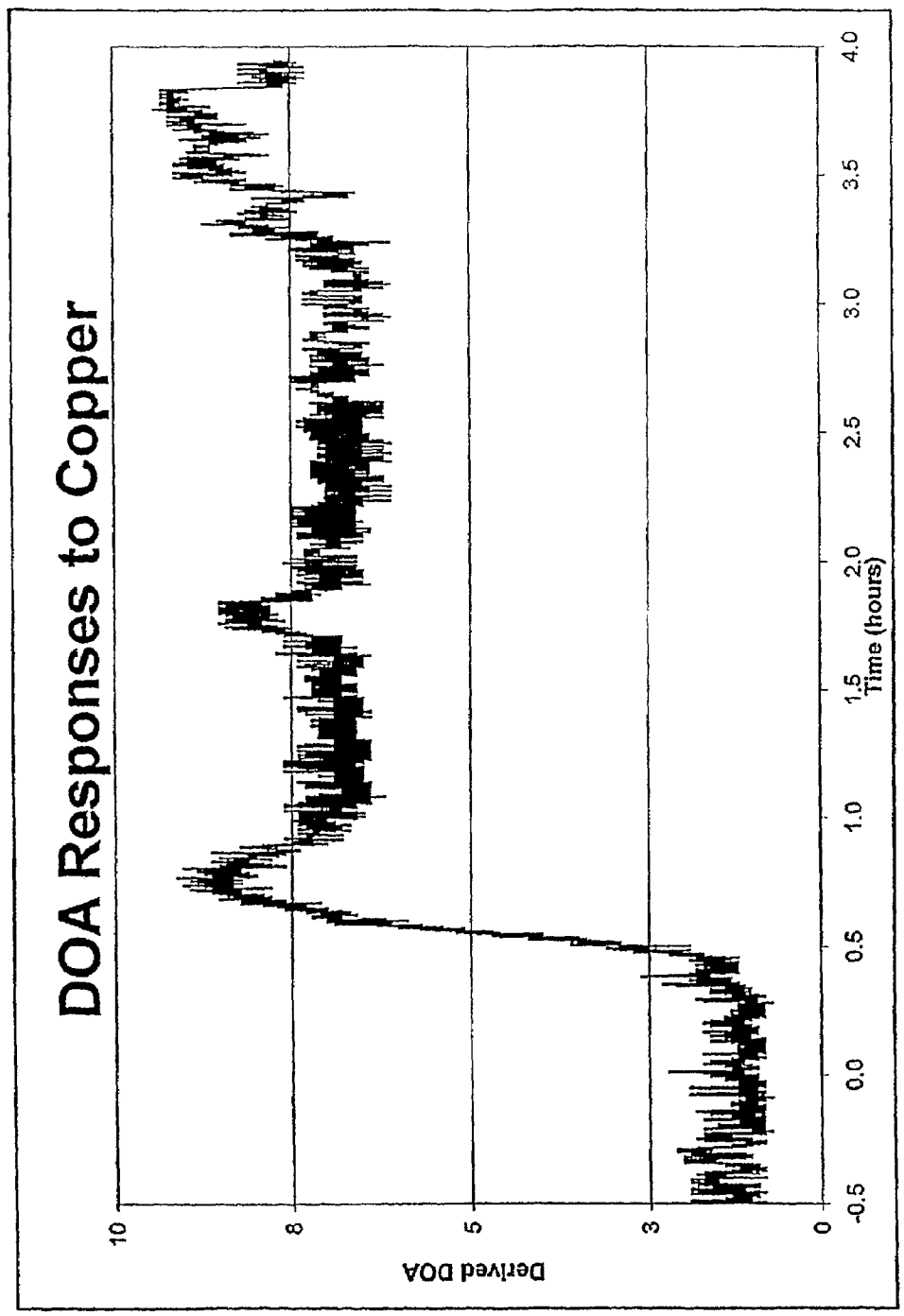

In this example, a system as in Example 3 was used, only the toxicant introduced was copper (as aqueous $CuSO_4$), as shown in FIG. 17. Raw percentage gape data (FIG. 18) was smoothed as a traveling mean gape (FIG. 19), and also was analyzed to yield traveling variance values, as seen in FIG. 20. The resulting DOA values, seen in FIG. 21, increase to exceed 8 out of a possible 10 between 0.5 and 1.0 hours, while the concentration of copper was still relatively low, and gape had only decreased to 50%.

Neural Net Embodiments

Detection of toxicants based on the mollusk output data may also be advantageously achieved using an artificial neural network. Particularly preferred for such an application is neural net software of the Neuralware Co., of Pittsburgh, Pa., although a variety of other software packages are suitable.

Figure 22:
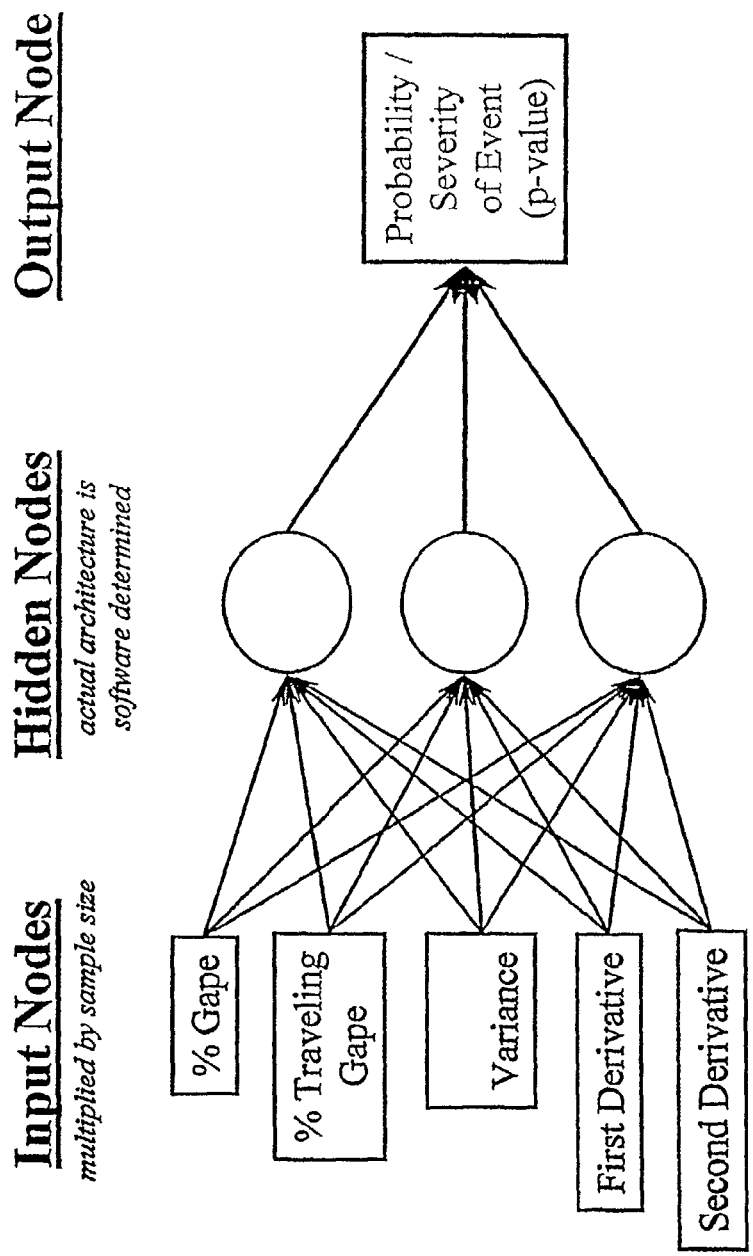
FIG. 22 is a generalized schematic of a neural net system for detecting toxicant presence.

As best seen in FIG. 22, the neural net system operates on a computer, either in the housing of system 3, or at a remote location. As with previously discussed embodiments, a system using a neural net to identify toxic events will include a FIFO stack of the last n values of percentage gape for the mollusk. The neural net has a number of input nodes which receive the mollusk output data in a relatively raw form, as percentage gape, and in other statistical forms related to earlier data, including traveling mean gape (the average percentage gape over the last n data samples), variance, and first and second derivatives, all discussed above. These input nodes forward these statistics to the hidden nodes of the system, which yield at an output node a value, which may be a DOA value as in the previous examples, or a p-value ranging from zero to 1, which represents the probability of a toxic event being in progress.

Training of such a neural net is performed once for the specific type of installation by exposing the mollusks to various toxicants in various concentrations, and also with data corresponding to the behavior of a mollusk in the absence, or substantial absence, of any toxicant. The neural net is also provided during training with corresponding DOA values so that the neural net can interpolate a relation therebetween. Once training has been done, the neural net nodes are defined as Flashcode or other code generated by the neural net software compiler. This neural net code can be incorporated into the existing software as an analytical routine and then can be selected in place of other DOA algorithms into the computer of any similar water screening system to process the mollusk data thereof.

Figure 23:
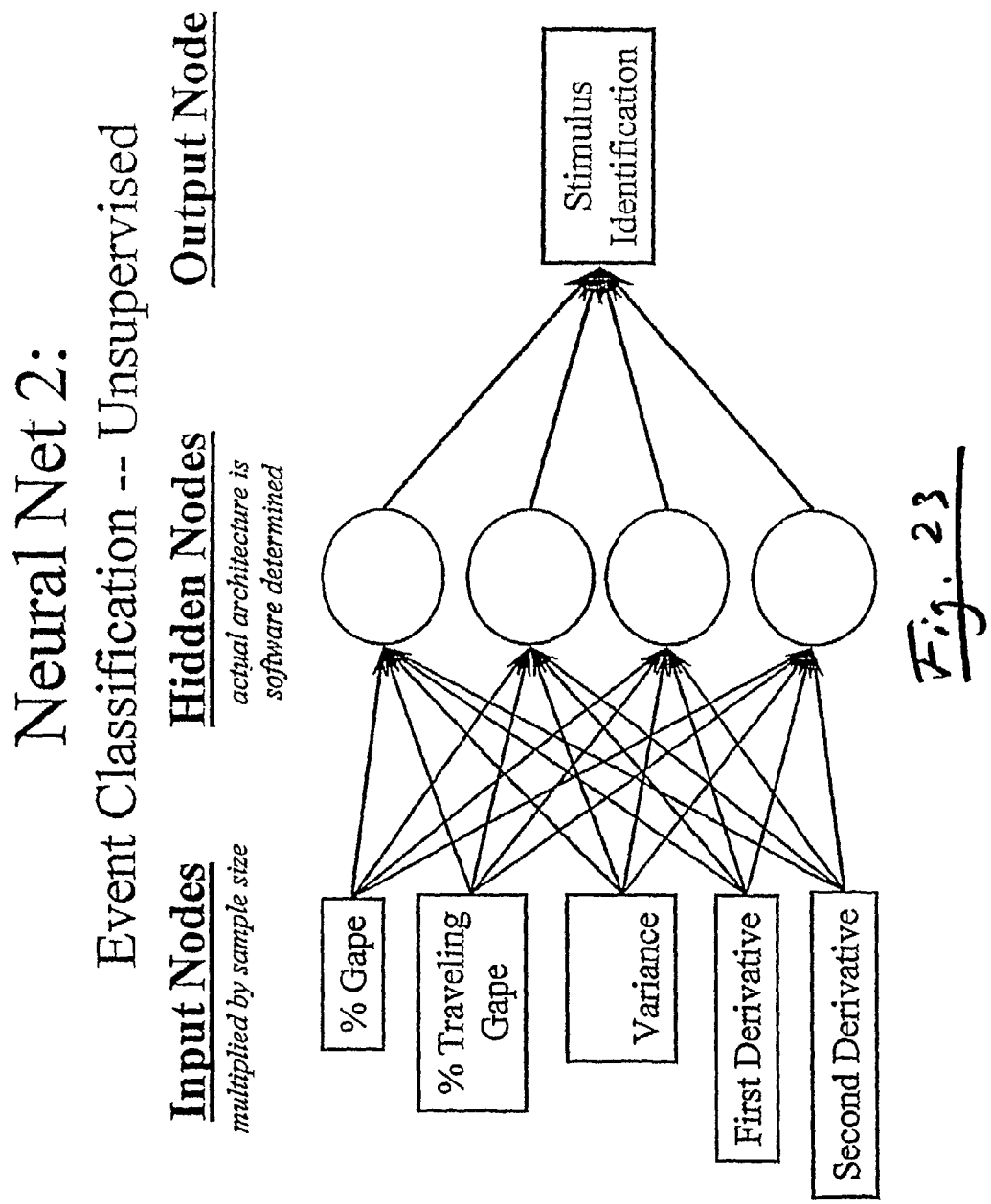
FIG. 23 is a generalized schematic of a neural net system for identifying a specific toxicant or type of toxicant present in the water being screened.

An additional enhancement is made possible by the fact that the behavior of mollusks in response to different toxicants may vary substantially. As a result, the toxicant to which the mollusk is exposed, in some cases, can be identified based on the mollusk's reaction. This is preferably also accomplished using a neural net, and such a neural net is shown schematically in FIG. 23.

The second neural net is provided with the same data as supplied to the input nodes of the first neural net, but the second neural net is trained to supply at its output node an output or value that identifies the stimulus, i.e., the specific toxicant or type of toxicant which has provoked the reactive behavior of the mollusk.

This second neural net is trained by exposing mollusks to a vast variety of toxicants, and supplying the output data of the mollusks to the neural net, together with identification of the toxicant or type of toxicant involved. Once the neural net has learned how to identify the differing toxicants, the neural net logic is loaded as Flashcode, or other code derived from the neural net software, into a computer in any similar or analogous mollusk-based system. Coupled with a p-value generated by the first neural net, such a system generates both the probability that a toxicant is present, and an identification of the toxicant.

It is to be understood that the calculations herein are preferably performed on a digital computer, and that the term value used herein refers to electronic data stored in data areas in the computer used which data areas are normally identified in the relevant software in the computer as variables. Also, the terms used herein should be read as descriptive rather than limiting, since those with knowledge in the art with this specification before them will be able to make modifications to the systems and methods therein without departing from the spirit of the invention.

What is claimed is:

1. A method for installing a mollusk having two shells in a chamber in a system for screening water for the presence of toxicants, said method comprising:
affixing an attachment portion to one of the shells of the mollusk;
connecting the attachment portion to a support assembly supported in the chamber, said attachment portion and support assembly being configured so that the attachment portion can be released from the support assembly, thereby releasing the mollusk when desired;
engaging the other shell of the mollusk with a sensing apparatus detecting a range of positions of the shell, said range of positions including at least a closed position, an open position and an intermediate position therebetween, and generating a periodic or continuous output signal indicative of the position of the shell, the sensing apparatus including a first movable lever having a pivot connection supporting the first movable lever in the chamber for pivoting movement responsive to movement of the shell, the detected position of the shell of the mollusk being dependent on the position of said movable lever, said movable lever having a proximal portion engaging the shell of the mollusk so as to move therewith when the mollusk opens and closes the shell, and a distal portion extending away from the proximal portion beyond the pivot connection, the sensing apparatus further including a biasing structure biasing the movable lever so that the proximal portion engages the shell, said biasing structure applying sufficiently small force to the movable lever such that the movable member does not substantially interfere with the opening or closing movement of the shell;
clamping the shells of the mollusk shut;
adjusting the sensing apparatus so that said sensing apparatus generates an output in a predetermined range to circuitry, which analyzes said signal such that said signal is as indicative of the gape of said mollusk; and
releasing the shells of the mollusk thereby installing a mollusk.

2. The method according to claim 1 and further comprising connecting the chamber to a system supplying the water to be screened so that said water flows through the chamber and at least partially submerges the mollusk.

3. The method according to claim 1 further including positioning the attachment portion relative to the shell of the mollusk using a structure that positions the attachment portion on a lateral centerline of the shell.

4. The method according to claim 1 further comprising adjusting the position of the mollusk in the chamber by adjusting positioning means of the attachment portion and/or the support assembly.

5. The method according to claim 4 and said adjusting including rotation of co-acting threaded portions of the positioning means to move the mollusk toward or away from the support assembly.

6. The method according to claim 1 further comprising monitoring the movement of the shell of the mollusk over a period of one day; and adjusting the relative position of a sensor in the sensing apparatus so that the sensing apparatus outputs a signal with a minimum and a maximum value in a predetermined range for processing said signals.

7. The method according to claim 1, further comprising monitoring the output of the sensing apparatus for a period of at least one day, and deriving from said output a value representing the maximum normal gape of the mollusk.

8. The method of claim 7, further includes determining for subsequent outputs of the sensing apparatus a percentage gape value derived from the subsequent output and the maximum normal gape value.

9. The method of claim 7, wherein the sensing apparatus is adjusted so that the output is approximately zero when the shell is clamped closed and increases as the shell opens.

10. A method for installing a mollusk having two shells in a chamber in a system for screening water for the presence of toxicants, said method comprising:
affixing an attachment portion to one of the shells of the mollusk;
connecting the attachment portion to a support assembly supported in the chamber, said attachment portion and support assembly being configured so that the attachment portion can be released from the support assembly, thereby releasing the mollusk when desired;
engaging the other shell of the mollusk with a sensing apparatus detecting a range of positions of the shell, said range of positions including at least a closed position, an open position and an intermediate position therebetween, and generating a periodic or continuous output signal indicative of the position of the shell, the sensing apparatus including a first movable member having a pivot connection supporting the first movable member in the chamber for pivoting movement responsive to movement of the shell, the detected position of the shell of the mollusk being dependent of the position of said movable member, said movable member having a proximal portion engaging the shell of the mollusk so as to move therewith when the mollusk opens and closes the shell, and a distal portion extending away form the proximal portion beyond the pivot connection, the sensing apparatus further including a biasing structure biasing the movable member so that the proximal portion engages the shell, said biasing structure applying a sufficiently small force to the movable member that the movable member does not substantially interfere with opening or closing movement of the shell;
clamping the shells of the mollusk shut;
adjusting the sensing apparatus so that said sensing apparatus generates an output in a predetermined range to circuitry analyzing said signal as indicative of gape of said mollusk; and
releasing the shells of the mollusk; and
wherein the sensing apparatus comprises first and second coacting parts supported in the sensing apparatus for movement of one of said first and second coacting parts relative to the other of said first and second coacting parts, said sensing apparatus producing an output dependent on a distance between said first and second coacting parts, said one of said first and second coacting parts of the sensing apparatus being connected with the movable member so that relative movement between the first and second coacting parts occurs, and said distance varies, when the movable member rotates with opening or closing movement of the shell.

11. A method as in claim 10, wherein the sensing apparatus constrains the relative movement of the first and second coacting parts such that reciprocation movement occurs therebetween in a predetermined path as the mollusk opens and closes the shell.

12. A method as in claim 11, wherein the predetermined path is an arc defined by said pivoting of the movable member.

13. A method as in claim 11, wherein the predetermined path is linear.

14. A method as in claim 12, wherein one of the first and second coacting parts of the sensor apparatus is a Hall effect transducer and the other of the first and second coacting parts of the sensor apparatus is magnet.

15. A method as in claim 13, wherein one of the first and second coacting parts of the sensor apparatus is a Hall effect transducer and the other of the first and second coacting parts of the sensor apparatus is a magnet.

16. A method for installing a mollusk having two shells in a chamber in a system for screening water for the presence of toxicants, said method comprising:
    securing one of the shells of the mollusk so as to be fixedly supported in the chamber;
    engaging the other shell of the mollusk with a sensing apparatus detecting a range of positions of the shell, said range of positions including at least a closed position, an open position and an intermediate position therebetween, and generating a periodic or continuous output signal indicative of the position of the other shell;
    the sensing apparatus including a first movable member engaging the other shell of the mollusk so as to move therewith and so that the detected position of the other shell of the mollusk is dependent on the position of said movable member;
    the sensing apparatus including a sensor system comprising first and second coacting sensor parts, the sensor system generating an electrical signal that varies dependent on an electromagnetic interaction over a distance between the two coacting sensor parts;
    said first coacting sensor part being supported fixedly with respect to the chamber, and the second coacting sensor part being supported on and being guided by a guide structure for relative reciprocating movement with respect to the chamber and with respect to the first coacting sensor part in a predetermined path determined by said structure;
    said movable member being operatively associated with the second coacting sensor part such that the second coacting sensor part moves in said relative reciprocating movement along said predetermined path of said guide structure when said movable member is moved by the other shell of the mollusk.

17. The method of claim 16 wherein one of the first and second coacting sensor parts comprises a magnet and the other of the first and second coacting sensor parts comprises a Hall effect sensor.

18. The method of claim 17 wherein said guide structure supporting the second sensor part constrains said second coacting sensor part to move in a linear path.

19. A method for installing a mollusk having two shells in a chamber in a system for screening water for the presence of toxicants, said method comprising:
    securing one of the shells of the mollusk so as to be fixedly supported in the chamber;
    engaging the other shell of the mollusk with a sensing apparatus detecting a range of positions of the shell, said range of positions including at least a closed position, an open position and an intermediate position therebetween, and generating a periodic or continuous output signal indicative of the position of the other shell;
    the sensing apparatus including a first movable member engaging the other shell of the mollusk so as to move therewith and so that the detected position of the other shell of the mollusk is dependent on the position of said movable member;
    the sensing apparatus including a sensor system comprising first and second coacting sensor parts, the sensor system generating a signal that is dependent on a distance between the two coacting sensor parts;
    said first coacting sensor part being supported fixedly with respect to the chamber, and the second coacting sensor part being supported on and being guided by a guide structure for relative reciprocating movement with respect to the chamber and with respect to the first coacting sensor part in a predetermined path determined by said structure;
    said movable member being operatively associated with the second coacting sensor part such that the second coacting sensor part moves in said relative reciprocating movement along said predetermined path of said guide structure when said movable member is moved by the other shell of the mollusk; and
    wherein the movable member is biased to engage the shell of the mollusk.

20. The method of claim 19, wherein said second coacting sensor part is biased to move in a direction along said path, and the movable member is connected with the second sensor so that the movable member is biased to engage the shell of the mollusk.

21. The method of claim 19, wherein the movable member is pivotally mounted in the chamber on a pivot structure, and said movable member has two opposing portions extending from respective sides of said pivot structure, one of said opposing portions engaging the mollusk shell and the other of the opposing portions being linking to the second sensor.

22. A method for installing a mollusk having two shells in a chamber in a system for screening water for the presence of toxicants, said method comprising:
    securing one of the shells of the mollusk so as to be fixedly supported in the chamber;
    engaging the other shell of the mollusk with a sensing apparatus detecting a range of positions of the shell, said range of positions including at least a closed position, an open position and an intermediate position therebetween, and generating a periodic or continuous output signal indicative of the position of the other shell;
    the sensing apparatus including a first movable member engaging the other shell of the mollusk so as to move therewith and so that the detected position of the other shell of the mollusk is dependent on the position of said movable member;
    the sensing apparatus including a sensor system comprising first and second coacting sensor parts, the sensor system generating a signal that is dependent on a distance between the two coacting sensor parts;
    said first coacting sensor part being supported fixedly with respect to the chamber, and the second coacting sensor part being supported on and being guided by a guide structure for relative reciprocating movement with respect to the chamber and with respect to the first coacting sensor part in a predetermined path determined by said structure;
    said movable member being operatively associated with the second coacting sensor part such that the second coacting sensor part moves in said relative reciprocating movement along said predetermined path of said guide structure when said movable member is moved by the other shell of the mollusk; and
    removing the mollusk form said chamber and securing a second mollusk in said chamber so that the movable member engages a moving shell of the second mollusk and the sensor system outputs data relating to a time varying gape of said second mollusk.

23. The method of claim 22, wherein the first and second mollusks are each secured to an attachment structure which is then secured to a support structure in the chamber fixedly supporting one of the shells of each the mollusk in the chamber.

* * * * *